United States Patent
Urnovitz

(12)
(10) Patent No.: US 6,344,317 B2
(45) Date of Patent: *Feb. 5, 2002

(54) DIAGNOSTIC DETECTION OF NUCLEIC ACIDS

(75) Inventor: Howard B. Urnovitz, San Francisco, CA (US)

(73) Assignee: Chronix Biomedical, Inc., San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/943,607

(22) Filed: Oct. 3, 1997

Related U.S. Application Data

(60) Provisional application No. 60/026,762, filed on Oct. 4, 1996.

(51) Int. Cl.[7] .......................... C12Q 1/68; C12P 19/34; C07H 21/04
(52) U.S. Cl. ................. 435/6; 435/91.2; 536/23.5; 536/24.1; 536/24.31; 536/24.32; 536/24.33
(58) Field of Search ................. 435/6, 5, 91.2; 536/23.5, 24.1, 24.31, 24.32, 24.33

(56) References Cited

U.S. PATENT DOCUMENTS

| | | | |
|---|---|---|---|
| 4,965,189 A | 10/1990 | Owerbach | 435/6 |
| 5,455,044 A | 10/1995 | Kim et al. | 424/450 |
| 5,534,438 A | 7/1996 | Hayden et al. | 435/320.1 |
| 5,639,600 A | * 6/1997 | McGrath | 435/5 |
| 6,001,987 A | * 12/1999 | Perron et al. | 536/23.72 |

FOREIGN PATENT DOCUMENTS

| | | | |
|---|---|---|---|
| WO | 97/09452 | * | 3/1997 |
| WO | 97/35589 | * | 10/1997 |

OTHER PUBLICATIONS

Erlich, H.A. et al. Science 252:1643–1651, Jun. 1991.*
Clements, G.B. et al. The Lancet 346:221–223, Jul. 1995.*
Neri, A. et al. J. Exp. Med. 170:1715–1725, Nov. 1989.*
Egger, D. et al. J. Clin. Microbiol. 33(6):1442–1447, Jun. 1995.*
Poyry, T. et al. J. Virol. 66(9):5313–5319, Sep. 1992.*
Loewenstein–Lichtenstein, Y. et al. Nature Medicine 1(10):1082–85, Oct. 1995.*
Gnatt, A. et al. Cancer Research 50(7):1983–1987, Apr. 1990.*
Ludlow, L. et al. J. Biol. Chem. 271(36):22076–22080, Sep. 1996.*
Wieczorek et al., "Isolation and characterization of an RNA–proteolipid complex associated with the malignant state in humans" *Proc. Natl. Acad. Sci. USA* 82:3455–3459, (1985).
Bess, Jr., et al., "Microvesicles are a source of contaminating cellular proteins found in purified HIV–1 Preparations," *Virology* (1997) 230: 134–144.
Lina, et al., Multicenter Evaluation of a commercially available PCR assay for diagnosing enterovirus infection in a panel of cerebrospinal fluid specimens. J. Clinical Microbiol. vol. 34, 3002, 3006 (1996).
Angel, et al. Early diagnosis of toxoplasmic encephalitis in AIDS patients by dot blot hybridization analysis. J. of Clinical Microbiol. vol. 30, 3286–3287 (1992).
Ledbetter, et al. Rapid isolation of DNA probes within specific chromosome regions by interspersed repetitive sequence polymerase chain reaction. Genomics vol. 6, 475–481 (1990).
Basik, et al. A rapid method to quantitate the major form of genomic instability in sporadic colorectal cancers. Proceedings of the American Assn. for Cancer Research. vol. 37, 545 (1996).
Ayyanathan, et al. A non–radioactive DNA diagnostic procedure for the detection of malarial infection: general application to genome with repetitive sequences. Molecular and Cellular Probes. vol. 9, 83–89 (1995).

* cited by examiner

*Primary Examiner*—Carla J. Myers
*Assistant Examiner*—Diana Johannsen
(74) *Attorney, Agent, or Firm*—Townsend and Townsend and Crew LLP

(57) ABSTRACT

This invention provides sensitive nucleic acid hybridization assay methods for the detection of target human nucleic acids in a biological sample, such as acellular fluids. The methods are particularly useful in early diagnosis of chronic illnesses.

21 Claims, 1 Drawing Sheet

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..16
      (D) OTHER INFORMATION: /note= "primer PG01"

(xi) SEQUENCE DESCRIPTION: SEQ ID NO:1:

AAGCACTTCT GTTTCC                                                   16

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..18
      (D) OTHER INFORMATION: /note= "primer PG02"

(xi) SEQUENCE DESCRIPTION: SEQ ID NO:2:

CATTCAGGGG CCGGAGGA                                               18

(2) INFORMATION FOR SEQ ID NO:3:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..19
      (D) OTHER INFORMATION: /note= "primer PG03"

(xi) SEQUENCE DESCRIPTION: SEQ ID NO:3:

GAATGTGTAA GAACTGTCA                                           19

(2) INFORMATION FOR SEQ ID NO:4:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (ix) FEATURE:

```
        (A) NAME/KEY: -
        (B) LOCATION: 1..22
        (D) OTHER INFORMATION: /note= "primer PG04"

(xi) SEQUENCE DESCRIPTION: SEQ ID NO:4:

GTAAACAATG TTTCTTTTAG CC                                              22

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "primer PG07"

(xi) SEQUENCE DESCRIPTION: SEQ ID NO:5:

CAGTTCAAGA GCAARCACC                                                  19

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "primer PG08"

(xi) SEQUENCE DESCRIPTION: SEQ ID NO:6:

TCRTCCATRA TMACYACWCC                                                 20

(2) INFORMATION FOR SEQ ID NO:7:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..357
        (D) OTHER INFORMATION: /note= "OPV clone #39"

(xi) SEQUENCE DESCRIPTION: SEQ ID NO:7:

AAGCACTTCT GTTTCCCCGG TGACATTGCA TAGACTGCTC ACGCGGTTGA AAGTGATCAA       60

TCCGTTACCC GCTTGTGTAC TTCGAAAAGC CTAGTATCGC CTTGGAATCT TCGACCGTTG      120

CGCTCAGCAC CCGACCCCGG GGTGTAGCTT AGGCTGATGA GTCTGACAT TCCTCACCGG       180

TGACGGTGGT CCAGGCTCAT CAGCCTAAGC TACACTCTGG GGTTGAGTGC TGAGCGCAAC      240

GCATCGAAGA TTCGGAGGTG GTACTGGGCT TCTCGAAGTA CATAAGCGGA TAACGGATCC      300

GTCGCTTTCA ACCACGCAAG CAGTCTATAC AACATCACCG GGGAAACAGA AGTGCTT        357
```

(2) INFORMATION FOR SEQ ID NO:8:

(i) SEQUENCE CHARACTERISTICS:
        (A) LENGTH: 458 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..458
        (D) OTHER INFORMATION: /note= "OPV clone #42"

(xi) SEQUENCE DESCRIPTION: SEQ ID NO:8:

```
AAGCACTTCT GTTTCCCACA GATCCTGCAG CACCGTTTGC GTTCCATTAA CGCCGCGTTC      60

AAACGTGCCA GGGAATCCTA CGGCTATAAC GGCGATTACT TCCTTGTTTA TCCGATCAAA     120

GTTAACCAGC ACCGCCGCGT GATTGAGTCC CTGATTCATT CGGGCGAACC GCTGGGTCTG     180

GAAGCCGGTT CCAAAGCCGA GTTGATGGCA GTACTGGCAC ATGCTGGCAT GACCCGTAGC     240

GTCATCGTCT GCAACGGTTA TAAAGACCGC GAATATATCC GCCTGGCATT AATTGGCGAG     300

AAGATGGGGC ACAAGGTCTA TCTGGTCATT GAGAAGATGT CAGAAATCGC CATTGTGCTG     360

GATGAAGCAG AACGTCTGAA TGTCGTTCCT CGTCTGGGCG TGCGTGCACG TCTGCTTCGC     420

AGGGTTCGGG TAAATGGCAG TCCTCCGGCC CCTGAATG                             458
```

(2) INFORMATION FOR SEQ ID NO:9:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..459
        (D) OTHER INFORMATION: /note= "OPV clone #43"

(xi) SEQUENCE DESCRIPTION: SEQ ID NO:9:

```
AAGCACTTCT GTTTCCCACA GATCCTGCAG CACCGTTTGC GTTCATTACG CCGCGTTCAA      60

ACGTGCCAGG GAATCCTACG GCTATAACGG CGATTACTTC CTTGTTTATC CGATCAAAGT     120

TAACCAGCAC CGCCGCGTGA TTGAGTCCCT GATTCATTCG GGCGAACCGC TGGGTCTGGA     180

AGCCGGTTCC AAAGCCGAGT TGATGGCAGT ACTGGCACAT GCTGGCATGA CCCGTAGCGT     240

CATCGTCTGC AACGGTTATA AGACCGCGA ATATATCCGC CTGGCATTAA TTGGCGAGAA     300

GATGGGGCAC AAGGTCTATC TGGTCATTGA GAAAATGTCA VAAATCGCCA TTGTGCTGGA     360

TGAAGCAGDA CGTCTGAATG TCGTTCCTCG TCTGGGCGTG SMGTCCACCT CTCCCTTCGC     420

AGGGGTTCGG GKAAAWDCCS CTCCTCCGGC CCCTGAATG                            459
```

(2) INFORMATION FOR SEQ ID NO:10:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: DNA (genomic)

(ix) FEATURE:

(A) NAME/KEY: -
        (B) LOCATION: 1..459
        (D) OTHER INFORMATION: /note= "OPV clone #45"

(xi) SEQUENCE DESCRIPTION: SEQ ID NO:10:

```
AAGCACTTCT GTTTCCCAMA GATCCTGCAG CACCGTTTGB GTTCCATTAA CGSCCGCGTT      60

CAAACGTGCC AGGGAATCCT ACGGCTATAA CGGCGATTAC TTCCTTGTTT ATCCGATCAA     120

AGTTAACCAG CACCGCCGCG TGATTGAGTC CCTGATTCAT TCGGGCGAAC CGCTGGGTCT     180

GGAAGCCGGT TCCAAAGCCG AGTTGATGGC AGTHCTGGCA CATGCTGGGC ATGACCCGTA     240

GCGTCATCGT CTGCAACGGT TATAAAGACC GCGAATATAT CCGCCTGGCA TTAATTGGCG     300

AGAAGATGGG GCACAAGGTC TATCTGGTCA TTGAGAAGAT GTCAGAAATC GCCATTGTGC     360

TGGATGAAGC AGAACGTCTG AATGTCGTTC CTCGTCTGGG CGTGVGTGCA CGTCTGSTTC     420

GCAGGGTTCG GGTAAATGCA GTCCTCCGGC CCCTGAATG                            459
```

(2) INFORMATION FOR SEQ ID NO:11:

(i) SEQUENCE CHARACTERISTICS:
        (A) LENGTH: 458 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..458
        (D) OTHER INFORMATION: /note= "OPV clone #46"

(xi) SEQUENCE DESCRIPTION: SEQ ID NO:11:

```
AAGCACTTCT GTTTCCCACA GATCCTGCAG CACCGTTTGC GTTCCATTAA CGCCGCGTTC      60

AAACGTGCCA GGGAATCTAC GGCTATAACG GCGATTACTT CCTTGTTTAT CCGATCAAAG     120

TTAACCAGCA CCGCCGCGTG ATTGAGTCCC TGATTCATTC GGGCGAACCG CTGGGTCTGG     180

AAGCCGGTTC AAAGCCGAG TTGATGGCAG TACTGGCACA TGCTGGCATG ACCCGTAGCG     240

TCATCGTCTG CAACGGTTAT AAAGACCGCG AATATATCCG CCTGGCATTA ATTGGCGAGA     300

AGATGGGGCA CAAGGTCTAT CTGGTCATTG AGAAGATGTC AGAAATCGCC ATTGTGCTGG     360

ATGAAGCAGA ACGTCTGAAT GTCGTTCCTC GTCTGGGCGT GCGTGCACGT CTGGCTTCGC     420

AGGGTTCGGG TAAATGGCAG TCCTCCGGCC CCTGAATG                             458
```

(2) INFORMATION FOR SEQ ID NO:12:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..414
        (D) OTHER INFORMATION: /note= "Subject #1 clone #7B"

(xi) SEQUENCE DESCRIPTION: SEQ ID NO:12:

```
CATTCAGGGG CCGGAGGACG TTTTGCTACA GCTGCTGTGG GCACAATTGC AGGCGCTGTA      60

TTAGCACCAA TCACAAGTGG TACGGCGTCC ACTGCTTGGT CAGGTATCTC AGGTTCTTCT     120

AACGCCTTGC AAGCGTCTAT GGATGAGAAC TTCGCTCAGG CTGCAGCTGT ACGTCGCAGA     180
```

```
GCAAGCGTTG CTGAAGCAGG AAAAACTGGG ATTCTGGCGT ACAGCAATGC GACTACTCCT      240

GGATCGAAGG TGACTATTGC GGTTTCTATG GCTTTTAACT GCAGCGTTGC CGGCGCATCT      300

GCAGATGCAT CCAGCTTGCA GGCAATTGTA GCGGCACCGG TCAATATGCC TAGTGGTTCA      360

GCCGTCACAC CAACATCGTT TCCGTCGGCT CCCGTGACAG TTCTTACACA TTTC            414
```

(2) INFORMATION FOR SEQ ID NO:13:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..414
        (D) OTHER INFORMATION: /note= "Subject #2 clone #8B2"

(xi) SEQUENCE DESCRIPTION: SEQ ID NO:13:

```
CATTCAGGGG CCGGAGGACG TTTTGCTACA GCTGCTGTGG GCACAATTGC AGGCGCTGTA       60

TTAGCACCAA TCACAAGTGG TACGGCGTCC ACTGCTTGGT CAGGTATCTC AGGTTCTTCT      120

AACGCCTTGC AAGCGTCTAT GGATGAGAAC TTCGCTCAGG CTGCAGCTGT ACGTCGCAGA      180

GCAAGCGTTG CTGAAGCAGG AAAAACTGGG ATTCTGGCGT ACAGCAATGC GACTACTCCT      240

GGATCGAAGG TGACTATTGC GGTTTCTATG GCTTTTAACT GCAGCGTTGC CGGCGCATCT      300

GCAGATGCAT CCAGCTTGCA GGCAATTGCA GCGGCACCGG TCAATATGCC TAGTGGTTCA      360

GCCGTCACAC CAACATCGTT TCCGTCGGCT CCCGTGACAG TTCTTACACA TTTC            414
```

(2) INFORMATION FOR SEQ ID NO:14:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..414
        (D) OTHER INFORMATION: /note= "Subject #2 clone #8B3"

(xi) SEQUENCE DESCRIPTION: SEQ ID NO:14:

```
CATTCAGGGG CCGGAGGACG TTTTGCTACA GCTGCTGTGG GCACAATTGC AGGCGCTGTA       60

TTAGCACCAA TCACAAGTGG TACGGCGTCC ACTGCTTGGT CAGGTATCTC AGGTTCTTCT      120

AACGCCTTGC AAGCGTCTAT GGATGAGAAC TTCGCTCAGG CTGCAGCTGT ACGTCGCAGA      180

GCAAGCGTTG CTGAAGCAGG AAAAACTGGG ATTCTGGCGT ACAGCAATGC GACTACTCCT      240

GGATCGAAGG TGACTATTGC GGTTTCTATG GCTTTTAACT GCAGCGTTGC CGGCGCATCT      300

GCAGATGCAT CCAGCTTGCA GGCAATTGCA GCGGCACCGG TCAATATGCC TAGTGGTTCA      360

GCCGTCACAC CAACATCGTT TCCGTCGGCT CCCGTGACAG TTCTTACACA TTTC            414
```

(2) INFORMATION FOR SEQ ID NO:15:

(i) SEQUENCE CHARACTERISTICS:
        (A) LENGTH: 414 base pairs
        (B) TYPE: nucleic acid (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..414
            (D) OTHER INFORMATION: /note= "Subject #3 clone #9B2"

(xi) SEQUENCE DESCRIPTION: SEQ ID NO:15:

```
CATTCAGGGG CCGGAGGACG TTTTGCTACA GCTGCTGTGG GCACAATTGC AGGCGCTGTA      60

TTAGCACCAA TCACAAGTGG TACGGCGTCC ACTGCTTGGT CAGGTATCTC AGGTTCTTCT     120

AACGCCTTGC AAGCGTCTAC GGATGAGAAC TTCGCTCAGG CTGCAGCTGT ACGTCGCAGA     180

GCAAGCGTTG CTGAAGCAGG AAAAACTGGG ATTCTGGCGT ACAGCAATGC GACTACTCCT     240

GGATCGAAGG TGACTATTGC GGTTTCTATG GCTTTTAACT GCAGCGTTGC CGGCGCATCT     300

GCAGATGCAT CCAGCTTGCA GGCAATTGCA GCGGCACCGG TCAATATGCC TAGTGGTTCA     360

GCCGTCACAC CAACATCGTT TCCGTCGGCT CCCGTGACAG TTCTTACACA TTTC           414
```

(2) INFORMATION FOR SEQ ID NO:16:

(i) SEQUENCE CHARACTERISTICS:
            (A) LENGTH: 414 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..414
            (D) OTHER INFORMATION: /note= "Subject #3 clone #9B4"

(xi) SEQUENCE DESCRIPTION: SEQ ID NO:16:

```
CATTCAGGGG CCGGAGGACG TTTTGCTACA GCTGCTGTGG GCACAATTGC AGGCGCTGTA      60

TTAGCACCAA TCACAAGTGG TACGGCGTCC ACTGCTTGGT CAGGTATCTC AGGTTCTTCT     120

AACGCCTTGC AAGCGTCTAT GGATGAGAAC TTCGCTCAGG CTGCAGCTGT ACGTCGCAGA     180

GCAAGCGTTG CTGAAGCAGG AAAAACTGGG ATTCTGGCGT ACAGCAATGC GACTACTCCT     240

GGATCGAAGG TGACTATTGC GGTTTCTATG GCTTTTAACT GCAGCGTTGC CGGCGCATCT     300

GCAGATGCAT CCAGCTTGCA GGCAATTGCA GCGGCACCGG TCAATATGCC TAGTGGTTCA     360

GCCGTCACAC CAACATCGTT TCCGTCGGCT CCCGTGACAG TTCTTACACA TTTC           414
```

(2) INFORMATION FOR SEQ ID NO:17:

(i) SEQUENCE CHARACTERISTICS:
            (A) LENGTH: 1218 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..1218
            (D) OTHER INFORMATION: /note= "Subject #1 clone #7A"

(xi) SEQUENCE DESCRIPTION: SEQ ID NO:17:

```
CATTCAGGGG CCGGAGGAGA AAGCCGAGCG ATTTAGGCTG ATGACAACAC ACGGGGTCAG      60

CGAGCTGGAT GCTGCAATGG TGGTGGCCAG ATCCATAGAC CAAAAGCGGA AATTATCCTG     120
```

```
TCTGACAGCG CTAGCTGTKG ATTTTCAATG ACCTAACAAA TATCAAAGGC CATTCATCCC        180

AATCACCACT TGATCGAGAC GCTTCACATC GGCGACCCGA CTAACTGAAG AAATATTTTC        240

GCAATGCTTG ACTTGAGTTG AATTTATCTC CCMCCAATGT TAAAAAGCCA GCGCCTACCC        300

AAGGCTCGCA TTTCTGAGGC GTAAACGCCT CAGCCTTGTA GCGCTTATTC CTTCGACTCT        360

TCGAGTCGGT TCGCCAGGTG GCCCTTGGCG ATGTTGGAGC CTTGGGCTAG GCACTCAATA        420

TCAAACACTC AAGGATTATG TGTATGTCGG CGCAGGATGC TGTTGATGAA AATTTGAATA        480

ACTATTCAAT TACAACCAAC AAAAGAACTT GCCGAGAGAC TTAAAACAAA ACCTTCAAAA        540

ATCTCTTTCT ATGCACACTA TTTACCTGAC AAGAAAAAAT ATAAAACACA TACAATTTCA        600

AAGCGCGGCG GTGGGGGGCG CCTTATAGAT GCGCCAAACA AAAATCTAAA AATAATTCAA        660

AGATCTATAG CTAACTTTTT AAACGAACAG TATAAAGCTC GCGCCTGCGT CTTCGCTTAT        720

GTTCAAAACC GAGGAATAGT AGGTCACGGC GAAGTGCACA CCAATCAAAG ATGGTTACTT        780

CGATTAGATA TCAAAGATTT CTTCCACTCA ATCACTACTG CACGTTTAAC AGGCCTCCTA        840

GTTGCCGCAC CGTTTTTCAT TGCCCCGAAT GTAGCAAGAA CTATAAGTTT GCTATGCACT        900

AAAGACGGGC GCTTACCTCA AGGCTCCCCA GCCAGCCCGA CAATTAGTAA TATTATATGT        960

CGAGGACTTG ACTACAAGCT CAAAACAATT GCATCTAAAA ATAAGTGTTA CTATACGCGT       1020

TATGCGGACG ACATATTCTT ATCCAATAAC GGCGCGATCT TTCCACCCTT CCTAGCGCAG       1080

AAAAACGATA AAGGCATCGT CACTATTGGA GTGGAGCTTA GTGAAATAAT AACGTCCGCC       1140

GGCTTTAGCA TAAACGAAGA AAAAACTTTT CTCAGAAGTA GGGGCGAACG TCAAATTGTG       1200

ACAGTTCTTA CACATTTC                                                    1218

(2) INFORMATION FOR SEQ ID NO:18:

(i) SEQUENCE CHARACTERISTICS:
        (A) LENGTH: 758 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..758
        (D) OTHER INFORMATION: /note= "Subject #1 clone #1B"

(xi) SEQUENCE DESCRIPTION: SEQ ID NO:18:

AAGCACTTCT GTTTCCAGTA ACAGCGATTG AGGTTTGACC TGGTCATCGG GGCGAAGTTC         60

CAAGGTGTAG AGCCCAGCTG GACCAAGGCT TGGGCTATCT GCTCATGCTC GAGCGGGTTG        120

CAAACCAGGG TGGCCTTCAT AGGTGGAATT TGCGTCGTTA CCAACTGTTT GACCAATGCC        180

GAAAGGGCTT TGGGGGAGGC ACTTCCTCCA ACAGGCAGTG GAAGGCTCGG TTGGCGATGG        240

ATGTTGCGTA GTGTTCGAGG TTGTCACACA TCGCCTTGCG TTGGCGCBCC CACGCACTGA        300

GTTGCGCGTG GGCGCGTGAC CAGAAGTCGA GGCGGGCCTK CTCAAGCATT TCTTCACGAT        360

GCTCAACCGC CTGGCGCAGA GGCTCTTCAG CTTGGGCCCG TGCGCTATCT AGCAACTGCG        420

CGGACTGAAA GCAATCGGCG AGCATCTCCC GGGTAATCAG TACTTTTGGC TGCCCGGAAG        480

CGCCGTCGTG CAATTCGATT TTGCGTTGGG TCAACATAGA CAATGCTCTG GTGTGTTGCC        540

GTTAACGACG AGTTGTTTCA CTACCCGTTG CGTCGATACG CCAGACAATC GCCTGCCACA        600

GCGTATTGAG CCGGCCATGC GCATCGTCAA ATGGCAGGTG TGTGGTTTCA AGTGCCTGCA        660
```

-continued

```
CCCGGTCAGG CGGCAAGCGC AGACGAAGGC GTTGCCAGAC AGCAGGCTCG ACCCAGGCCC    720

TCAGCAATTG CATTGGATCA TCCTCCGGCC CCTGAATG                            758
```

(2) INFORMATION FOR SEQ ID NO:19:

(i) SEQUENCE CHARACTERISTICS:
        (A) LENGTH: 760 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..760
        (D) OTHER INFORMATION: /note= "Subject #2 clone #2B"

(xi) SEQUENCE DESCRIPTION: SEQ ID NO:19:

```
AAGCACTTCT GTTTCCAGTA ACAGCGATTG AGGTTTGACC TGGTCATCGG GGCGAAGCTT     60

CCAAGGTGTA GAGCCCAGCT GGACCAAGGC TTGGGCTATC TGCTCATGCT CGAGCGGGTT    120

GCAAACCAGG GTGGCCTTCA TAGGTGGAAT TTGCGTCGTT ACCAACTGTT TGACCAATGC    180

CGAAAGGCGC TTTGGGGGAG GCACTTCCTC CAACAGGCAG TGGAAGSCTC GGTTGGCGAT    240

GGATGTTGCG TAGTGTTCGA GGTTGTCACA CATCGCCTTG CGTTGGCGCT CCCACGCACT    300

GAGTTGCGCG TGGGCGCGTG ACCAGAAGTC GAGGCGGGCC TGCTCAAGCA TTTCTTCACG    360

ATGCTCAACC GCCTGGCGCA GCAGCTCTTC AGCTTGGGCC CGTGCGCTAT CTAGCAACTG    420

CGCGGACTGA AAGCAATCGG CGAGCATCTC CCGGGTAATC AGTACTTTTG GCTGCCCGGA    480

AGCGCCGTCG TGCAATTCGA TTTTGCGTTG GGTCAACATA GACAATGCTC TGGTGTGTTG    540

CCGTTAACGA CGAGTTGTTT CACTACCCGT TGCGTCGATA CGCCAGACAA TCGCCTGCCA    600

CAGCGTATTG AGCCGGCCAT GCGCATCGTC AAATGGCAGG TGTGTGGTTT CAAGTGCCTG    660

CACCCGGTTA GCGGCAAGC GCAGACGAAG GCGTTGCCAG ACAGCAGGCT CGACCCAGGC    720

CCTCAGCAAT TGCATTGGAT CATCCTCCGG CCCCTGAATG                          760
```

(2) INFORMATION FOR SEQ ID NO:20:

(i) SEQUENCE CHARACTERISTICS:
        (A) LENGTH: 759 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..759
        (D) OTHER INFORMATION: /note= "Subject #3 clone #3B"

(xi) SEQUENCE DESCRIPTION: SEQ ID NO:20:

```
AAGCACTTCT GTTTCCAGTA ACAGCGATTG AGGTTTGACC TGGTCATCGG GGCGAAGTTC     60

CAAGGTGTAG AGCCCAGCTG GACCAAGGCT TGGGCTATCT GCYCATGCTC GAGCGGGTTG    120

CAAACCAGGG TGGCCTTCAT AGGTGGAATT TGCGTCGTTA CCAACTGTTT GGCCAATGCC    180

GAAAGGCGCT TTGGGGGAGG CACTTCCTCC AACAGGCAGT GGAAGGCTCG GTTGGCGATG    240

GATGTTGCGT AGTGTTCGAG GTTGTCACAC ATCGCCTTGC GTTGGCGCYC CCACGCACTG    300

AGTTGCGCGT GGGCGCGTGA CCAGAAGTCG AGGCGGGCCT GCTCAAGCAT TTCTTCACGA    360

TGCTCAACCG CCTGGCGCAG CAGCTCTTCA GCTTGGGCCC GTGCGCTATC TAGCAACTGC    420
```

```
GCGGACTGAA AGCAATCGGC GAGCATCTCC CGGGTAATCA GTACTTTTGG CTGCCCGGAA      480

GCGCCGTCGT GCAATTCGAT TTTGCGTTGG GTCAACATAG ACAATGCTCT GGTGTGTTGC      540

CGTTAACGAC GAGTTGTTTC ACTACCCGTT GCGTCGATAC GCCAGACAAT CGCCTGCCAC      600

AGCGTATTGA GCCGGCCATG CGCATCGTCA AATGGCAGGT GTGTGGTTTC AAGTGCCTGC      660

ACCCGGTCAG GCGGCAAGSG CAGACGAAGG CGTTGCCAGA CAGCAGGCTC GACCCAGGCC      720

CTCAGCAATT GCATTGGATC ATCCTCCGGC CCCTGAATG                             759

(2) INFORMATION FOR SEQ ID NO:21:

(i) SEQUENCE CHARACTERISTICS:
        (A) LENGTH: 542 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..542
        (D) OTHER INFORMATION: /note= "Subject #2 clone #5B"

(xi) SEQUENCE DESCRIPTION: SEQ ID NO:21:

GAAATGTGTA AGAACTGTCA TGCCTGCGTA AGGTTGCTCC GACAGATGTA ACCTCCCATG      60

GAAATGTGAC ATTTTACTGC GGCGCCGCTT GTTCATCGGC GCCAAAGTCC CGGCACCGCC     120

CTCGCAGAAA TGATTAATAA ACAATCAATA AAGGGCTATT AACCCCGAGC AATGCTAAAC     180

TGAGGCTCCT TACATCTACC CGGTGAAAGA TATGTCTATC TTTGATGCCC TTAAGATGTT     240

CAGCGACTCA TCAGTAAAAG TGACCTGCCC GAAATGCGCT CACGTATCTG AACAAAACAG     300

TCGCAAAATG CGTAAAAACA TCACCATGAT CTGCCCTAAA TGSCGGCACT ATTTCCTTCC     360

TGACGACAAC TAACGCCTTT CTCTTTCTCT GCTGCAGTGT CAAACGCAAG CGTAACGTCA     420

CTGTTTATCC GGCAAGCGAG CCAACAGCAG TTCTCGCCGC CGTCCGCTGA ATACTTCAG      480

CATCAGCGCC AGGCAAACCA ACCAGGCAGG GATCAGCAAC AGGCTAAAAG AAACATTGTT     540

AC                                                                    542

(2) INFORMATION FOR SEQ ID NO:22:

(i) SEQUENCE CHARACTERISTICS:
        (A) LENGTH: 647 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..647
        (D) OTHER INFORMATION: /note= "Subject #1 clone #4B"

(xi) SEQUENCE DESCRIPTION: SEQ ID NO:22:

GAAATGTGTA AGAACTGTCA TTCACACTAC GGAGAGCCTG CGCCTTGGAT TGGCCCACCC      60

TGCTAACCCG CGAACGTCTT GGAAAACCCC TGCACAGCCC TGAAGAACTG GGCCGCAGCC     120

CCTTCCACAA AGATCACGAC CGCATTATTT TCTGCCGGCG CATTCCGGCG CCTGGGACGC     180

AAGACCCAAG TGCATCCGGT TTCGAGCAAC GACCATATCC ACACACGCTT GACCCACTCC     240

CTGGAAGTCA GCTGCGTGGG GCGCTCACTC GGCATGCGCG TGGGCGAAAC CCTGCGCAGC     300
```

```
GCCCTGCCCG ACTGGTGCGA CCCCAGCGAC CTGGGCATGG TGGTGCAATC GGCCTGCCTG      360

GCCCATGACA TCGGCAACCC GCCATTCGGG CATTCCGGCG AAGACGCCAT TCGCCACTGG      420

TTCCAACAGG CCGCCGGGCG AGGTTGGCTG GATGGCATGA GCAGCGCCGA ACGCAATGAC      480

TTCCTTAACT TCGAAGGCAA TGCCCAGRGC TTTCGGGTAC YCACCCAACT TGAATACCAC      540

CAGTTCGACG GCGGCACSGG CTGACCTACG CCACCTTGGG CACGTACCTC AAATACCCCT      600

GGACTGCCCG TCACGCCGAC TYGCTGGGCT AAAAGAAACA TTGTTAC                    647
```

(2) INFORMATION FOR SEQ ID NO:23:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..713
        (D) OTHER INFORMATION: /note= "clone 60"

(xi) SEQUENCE DESCRIPTION: SEQ ID NO:23:

```
AAGCACTTCT GTTTCCTGAA TCTAAAGAAA GACAACATGC TGCTTTTTAA TCATAGGATG       60

GAGAATTTTA AGAACTGTT  TGGGCCAGGC ACAGTCGCTC ATACTTGTAA TCCCAGCACT      120

TTGGGAGGCC GAGGCGGGTG GATCACAAGG TCAGCAGATC GAGACCATCC TGGCCAACAT      180

GGTGAAACCC TGTCTCTACT AAAAATACAA AAATTAGCCG GGTGTGGTGG CACATGCCTG      240

TAATCCCAGC TACTCGGGAA GCTGAGGCAG GAGAATTGCT TGAACCAGGG AGTTGGAGGT      300

TGCAGTGAGC TAAGACTGCA CCACTGCACT CCAGCCTGGT GACAGAACGA GACTCTGTCT      360

TAAAAACAAA CAAACAAAAA AAAAATCTGT TAGATAGGCT ATCAAAATGC AGCTGTTGTT      420

TTGTTTTTGG CTCACTGTTT TCGTGGTTGT AACTAATATG TGGAAAGGCC CATTTCCAGG      480

TTTGCGTAGA AGAGCCCAGA AAACAGAGTC TCAAGACCCC CGCTCTGGAC TGTCATAAGC      540

TAGCACCCGT GGTAAGCGGG ACGAGACAAG CTCCCGAAGC CCGCCAGCTT CCTGCTCCAC      600

TCAGCTCCGT CCAGTCAACC TGAACCCACC CAGTCCAGCT GTCTGTGGGA ATGGTGGTGT      660

TCTTAGGGAC AGACTGACAC CTTACTTGTC AGTGTTCCTC CGGCCCCTGA ATG            713
```

(2) INFORMATION FOR SEQ ID NO:24:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..713
        (D) OTHER INFORMATION: /note= "clone 61"

(xi) SEQUENCE DESCRIPTION: SEQ ID NO:24:

```
AAGCACTTCT GTTTCCTGAA TCTAAAGAAA GACAACATGC TGCTTTTTAA TCATAGGATG       60

GAGAATTTTA AGAACTGTT  TGGGCCAGGC ACAGTCGCTC ATACTTGTAA TCCCAGCACT      120

TTGGGAGGCC GAGGCGGGTG GATCACAAGG TCAGCAGATC GAGACCATCC TGGCCAACAT      180

GGTGAAACCC TGTCTCTACT AAAAATACAA AAATTAGCCG GGTGTGGTGG CACATGCCTG      240
```

```
TAATCCCAGC TACTCGGGAA GCTGAGGCAG GAGAATTGCT TGAACCAGGG AGTTGGAGGT      300

TGCAGTGAGC TAAGACTGCA CCACTGCACT CCAGCCTGGT GACAGAACGA GACTCTGTCT      360

TAAAAACAAA CAAACAAAAA AAAAATCTGT TAGATAAGCT ATCAAAATGC AGCTGTTGTT      420

TTGTTTTTGG CTCACTGTTT TCGTGGCTGT AACTAATATG TGGAAAGGCC CATTTCCAGG      480

TTTGCGTAGA AGAGCCCAGA AAACAGAGTC TCAAGACCCC CGCTCTGGAC TGTCATAAGC      540

TAGCACCCGT GGTAAGCGGG ACGAGACAAG CTCCCGAAGC CCGCCAGCTT CCTGCTCCAC      600

TCAGCTCCGT CCAGTCAACC TGAACCCACC CAGTCCAGCT GTCTGTGGGA ATGGTGGTGT      660

TCTTAGGGAC AGACTGACAC CTTACTTGTC AGTGTTCCTC CGGCCCCTGA ATG            713
```

(2) INFORMATION FOR SEQ ID NO:25:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..713
        (D) OTHER INFORMATION: /note= "clone 62"

(xi) SEQUENCE DESCRIPTION: SEQ ID NO:25:

```
AAGCACTTCT GTTTCCTGAA TCTAAAGAAA GACAACATGC TGCTTTTTAA TCATAGGATG       60

GAGAATTTTA AAGAACTGTT TGGGCCAGGC ACAGTCGCTC ATACTTGTAA TCCCAGCACT      120

TTGGGAGGCC GAGGCGGGTG GATCACAAGG TCAGCAGATC GAGACCATCC TGCCCAACAT      180

GGTGAAACCC TGTCTCTACT AAAAATACAA AAATTAGCCG GGTGTGGTGG CACATGCCTG      240

TAATCCCAGC TACTCGGGAA GCTGAGGCAG GAGAATTGCT TGAACCAGGG AGTTGGAGGT      300

TGCAGTGAGC TAAGACTGCA CCACTGCACT CCAGCCTGGT GACAGAACGA GACTCTGTCT      360

TAAAAACAAA CAAACAAAAA AAAAATCTGT TAGATAAGCT ATCAAAATGC AGCTGTTGTT      420

TTGTTTTTGG CTCACTGTTT TCGTGGTTGT AACTAATATG TGGAAAGGCC CATTTCCAGG      480

TTTGCGTAGA AGAGCCCAGA AAACAGAGTC TCAAGACCCC CGCTCTGGAC TGTCATAAGC      540

TAGCACCCGT GGTAAGCGGG ACGAGACAAG CTCCCGAAGC CCGCCAGCTT CCTGCTCCAC      600

TCAGCTCCGT CCAGTCAACC TGAACCCACC CAGTCCAGCT GTCTGTGGGA ATGGTGGTGT      660

TCTTAGGGAC AGACTGACAC CTTACTTGTC AGTGTTCCTC CGGCCCCTGA ATG            713
```

(2) INFORMATION FOR SEQ ID NO:26:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..713
        (D) OTHER INFORMATION: /note= "clone 64"

(xi) SEQUENCE DESCRIPTION: SEQ ID NO:26:

```
AAGCACTTCT GTTTCCTGAA TCTAAAGAAA GACAACATGC TGCTTTTTAA TCATAGGATG       60
```

-continued

| | | | | | |
|---|---|---|---|---|---|
| GAGAATTTTA | AAGAACTGTT | TGGGCCAGGC | ACAGTCGCTC | ATACTTGTAA | TCCCAGCACT | 120 |
| TTGGGAGGCC | GAGGCGGGTG | GATCACAAGG | TCAGCAGATC | GAGACCATCC | TGGCCAACAT | 180 |
| GGTGAAACCC | TGTCTCTACT | AAAAATACAA | AAATTAGCCG | GGTGTGGTGG | CACATGCCTG | 240 |
| TAATCCCAGC | TACTCGGGAA | GCTGAGGCAG | GAGAATTGCT | TGAACCAGGG | AGTTGGAGGT | 300 |
| TGCAGTGAGC | TAAGACTGCG | CCACTGCACT | CCAGCCTGGT | GACAGAACGA | GACTCTGTCT | 360 |
| TAAAAACAAA | CAAACAAAAA | AAAAATCTGT | TAGATAAGCT | ATCAAAATGC | AGCTGTTGTT | 420 |
| TTGTTTTTGG | CTCACTGTTT | TCGTGGTTGT | AACTAATATG | TGGAAAGGCC | CATTTCCAGG | 480 |
| TTTGCGTAGA | AGAGCCCAGA | AAACAGAGTC | TCAAGACCCC | CGCTCTGGAC | TGTCATAAGC | 540 |
| TAGCACCCGT | GGTAAGCGGG | ACGAGACAAG | CTCCCGAAGC | CCGCCAGCTT | CCTGCTCCAC | 600 |
| TCAGCTCCGT | CCAGTCAACC | TGAACCCACC | CAGTCCAGCT | GTCTGTGGGA | ATGGTGGTGT | 660 |
| TCTTAGGGAC | AGACTGACAC | CTTACTTGTC | AGTGTTCCTC | CGGCCCCTGA | ATG | 713 |

DIAGNOSTIC DETECTION OF NUCLEIC ACIDS

CROSS-REFERENCE TO RELATED APPLICATIONS

This application claims the benefit of U.S. Provisional Application No. 60/026,762, filed Oct. 4, 1996.

FIELD OF THE INVENTION

The invention relates to the detection of nucleic acids associated with disease states. In particular, the invention provides for the detection of nucleic acids in acellular biological fluids as diagnostic assays for chronic illnesses and infectious diseases. Also provided are therapeutic approaches to treating chronic illnesses.

BACKGROUND OF THE INVENTION

Chronic diseases such as cancer, autoimmune diseases, chronic fatigue syndrome and the like afflict millions of people throughout the world. It is known that environmental and other factors (e.g., genotoxic compounds, infectious retroviruses, retroelements and the like) can directly disrupt and/or damage DNA and may play a role in the development of a number of chronic illnesses. The mechanisms by which damage to genetic material leads to the onset of these diseases is not well understood, however. It is known that certain sites in the genome (e.g., fragile sites) are particularly susceptible to such modifications. For instance, it is known that the distribution of insertion sites for retroviruses and retroelements is not random and that fragile sites are often preferred (see, e.g., Craigie *Trends in Genetics* 8:187 (June 1992); De Ambrosis et al. *Cancer Genet. Cytogenet.* 60:1–7 (1992); Durnam et al. and Romani et al. *Gene* 135:153–160 (1993)).

Fragile sites themselves are associated diseases. For instance, expansion of long of blocks of repeated CCG triplets together with methylation of CpG islands in particular fragile sites on the X chromosome have been linked to the fragile X syndrome, an inherited mental retardation (see, e.g., Sutherland and Richards, *Proc. Nat. Acad. Sci. USA* 92:3636–3641 (1995).

The detection of nucleic acids from pathogens such as bacteria, parasites and viruses, is a commonly used method for diagnosis of disease. For instance, detection of viral sequences is useful in diagnosis of disease. Enteroviruses are a heterogeneous group of human pathogens and opportunistic agents responsible for a broad spectrum of diseases and make up a large genus within the family Picornaviridae. The genus includes polioviruses, coxsackieviruses, echoviruses as well as a number of uncharacterized enteroviruses isolated from humans and other primates. For a review of taxonomy of Picornaviridae see, *Virus Taxonomy: Classification and Nomenclature of Viruses* Murphy et al., eds (Springer Verlag, 1995).

Like other members of the picornaviridae, enteroviruses are small, single-stranded, nonenveloped RNA viruses. Enteroviruses are distinguished from other members of the picornaviridae by their stability in acid and their fecal-oral route of passage and transmission.

Polioviruses (which exist as at least three serotypes) are the most clinically significant of the enteroviruses worldwide, causing paralytic disease in children in developing countries. Non-polioenteroviruses (NPEV) are also responsible for large numbers of symptomatic infections each year. They are the most common etiologic agents of a number of illnesses including meningitis and nonspecific febrile illnesses. Recent reports have linked NPEV infection with chronic fatigue syndrome (Clements et al. *J. Med. Virol.* 45:156–161(1995).

In developed countries, polioviruses have been controlled with the introduction of vaccines in the late 1950's. Vaccines typically contain either inactivated poliovirus, which is administered parenterally or live attenuated poliovirus, which is administered orally. The inactivated vaccines use tissue culture-derived poliovirus which has been inactivated, or killed with formaldehyde. Attenuated virus vaccines are prepared by passage of the virus in cell cultures until it loses its ability to cause the disease. Attenuated live virus replicates in the gut to induce a protective antibody response.

Virus used for these vaccines is typically cultured in African Green Monkey kidney cells. As noted above, a number of poorly characterized enteroviruses have been isolated from primates, including monkeys. Procedures are currently in place to identify monkey cells infected by other viruses (e.g., SV40) before use in culturing polioviruses.

Understanding how these molecular changes lead to disease is not well understood in the art. Increased understanding of the cellular mechanisms, particularly changes in nucleic acids, that occur early in the pathogenesis of these diseases is important to development of useful therapies and diagnostic tools. In addition, identification of viruses, including enteroviruses, in polio vaccine preparations is important to ensure safety of polio vaccines. Moreover, the possibility that new viruses resulting from recombination of poliovirus with other viruses from the monkey cells or the human gut is an obvious public health concern. The present invention addresses these and other concerns.

SUMMARY OF THE INVENTION

The present invention provides methods of screening for a disease state in a patient. The methods comprise providing a sample containing biological material (e.g., biopsies) or biological fluids from the patient (e.g., an acellular biological fluid such as serum or plasma) and contacting the sample with a nucleic acid which specifically hybridizes to a target nucleic acid sequence. The target nucleic acids are then detected. In some embodiments, the target nucleic acid includes sequences from a fragile site in the human genome, in particular, repetitive DNA. In some embodiments the target sequences are derived from Alu sequences in a fragile site. In other embodiments, the target nucleic acid may be a novel composite of microbial origin and in some cases human origin. The target nucleic acid is usually at least about 100 nucleotides in length, sometimes between about 500 and about 1500 nucleotides in length.

The methods are usually used to detect a chronic illness. Examples of chronic illnesses include cancers, such as multiple myeloma. Other diseases include autoimmune diseases, neurodegenerative diseases, heart diseases and the like.

In certain preferred embodiments, the target human nucleic acids are amplified (e.g., by PCR). An exemplary target sequence is provided in SEQ ID NO:23. This sequence can be used in diagnosis of multiple myeloma.

The present invention further provides improved methods for detecting viral nucleic acids in biological samples and polio vaccine preparations. In one embodiment, the invention provides methods for detecting recombinant viral nucleic acids, which comprise nucleic acid sequences from a polio virus and a non-poliovirus, usually a non-polioenterovirus. The methods comprise contacting a biological sample suspected of containing the recombinant viral nucleic acid with a first primer which specifically hybridizes to a conserved sequence in a picornaviral genome and a second primer which specifically hybridizes to a poliovirus nucleic acid sequence. The presence of an amplified product which is a recombinant viral nucleic acid is then detected.

A number of primers may be used in the present invention. For instance, one or both the primers may be one that specifically hybridizes to a 5' nontranslated region of an picornaviral genome. Since the 5' nontranslated region is conserved among picornaviruses, the primer will specifically hybridize to most picornaviruses, particularly enteroviruses. Primers PG01 and PG02 (as shown in SEQ ID NO:1 or SEQ ID NO:2 are conveniently used for this purpose. One or both of the primers may specifically hybridize to a P2–P3 region of a poliovirus genome. A preferred primer is one that specifically hybridizes to nucleotides 4922–4941 or nucleotides 5467–5487. Primers PG03 and PG04 (as shown in SEQ ID NO:3 or SEQ ID NO:4) are conveniently used for this purpose. One or both of the primers may also specifically hybridize to a P2 region of a poliovirus genome. A preferred primer is one that specifically hybridizes to nucleotides 4460–4478 or nucleotides 4634–4653. Primers PG07 and PG08 (as shown in SEQ ID NO:5 or SEQ ID NO:6) are conveniently used for this purpose. A preferred combination of primers is PG02 and PG03.

The methods may be carried out using a number of biological samples commonly used for clinical analysis of nucleic acids. A convenient sample is human serum, plasma, or white blood cells.

A number of methods may be used to detect the presence of the recombinant viral nucleic acid. In some embodiments, the detection is carried out using gel electrophoresis to identify an amplified fragment that is not present in a control sample known to contain only poliovirus nucleic acids. When the first primer selectively hybridizes to nucleotides 443–460 of a poliovirus genome (e.g., PG02) and the second primer selectively hybridizes to nucleotides 4922–4941 of a poliovirus genome (e.g., PG03) an amplified fragment of about 400 nucleotides in length can be used to detect the presence of a recombinant viral nucleic acid.

The invention also provides methods for detecting nonpoliovirus nucleic acids in a polio vaccine sample. The methods comprise contacting the vaccine sample with at least two primers which specifically hybridize to poliovirus nucleic acid sequences.

In these methods, one primer can be one that specifically hybridizes to a conserved sequence in an enteroviral genome, such as the 5' nontranslated region. Exemplary primers include those that specifically hybridize to nucleotides 163–178 or nucleotides 443–450. Such primers include PG01 and PG02 (as shown in. SEQ ID NO:1 and SEQ ID NO:2).

A primer can also be one that specifically hybridizes to a sequence specific to a poliovirus genome, such as P2–P3 region of a poliovirus genome, for example, nucleotides 4922–4941 or nucleotides 5467–5487. Such primers include PG03 and PG04 (as shown in SEQ ID NO:3 and SEQ ID NO:4).

A primer can also be one that specifically hybridizes to a sequence specific to a poliovirus genome, such as the P2 region of a poliovirus genome, for example, nucleotides 4460–4478 or nucleotides 4634–4653. Such primers include PG07 and PG08 (as shown in SEQ ID NO:5 and SEQ ID NO:6).

In these methods, nonpoliovirus nucleic acids may be detected using gel electrophoresis to identify an amplified fragment that is not present in a control vaccine sample known to contain only poliovirus nucleic acids.

The invention further provides nucleic acid molecules from new, recombinant viruses identified here. The claimed molecules can be identified by their ability to hybridize to the exemplified sequences under stringent conditions, as defined below. The nucleic acids may be a complete viral genome, or fragments thereof. The nucleic acids may be isolated from a biological sample and may or may not be integrated in human chromosomal DNA.

Definitions

An "acellular biological fluid" is a biological fluid which substantially lacks cells. Typically, such fluids are fluids prepared by removal of cells from a biological fluid that normally contains cells (e.g., whole blood). Exemplary processed acellular biological fluids include processed blood (serum and plasma), urine, saliva, sweat, tears, phlegm, cerebrospinal, semen, feces and the like.

An "archived nucleic acid sequence" is a chimeric sequence in human genomic DNA containing subsequences from other organisms, particularly pathogens such as bacteria (e.g., members of the genera Chlamydia, Mycoplasma, Neisseria, Treponema, Staphylococcus, Streptococcus, and the like), parasites (e.g., *Plasmodium falciparum, Pneumocystis carinii*, Trichomonas, Cryptosporidium), viruses (e.g., herpes viruses, enteroviruses, polyoma viruses, poxviruses, such as Molluscum contagiosum viruses, retroviruses, such as HIV, and the like). Thus, when designing nucleic acids (e.g., as probes or PCR primers) for detecting archived nucleic acids of the invention, sequences based on the genome of these pathogens are conveniently used. Without wishing to be bound by theory, it is believed that archived nucleic acid sequences are usually inserted at fragile sites.

The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, serum, plasma, blood cells (e.g., white cells), tissue or fine needle biopsy samples, urine, peritoneal fluid, and pleural fluid, or cells therefrom. Biological samples may also include sections of tissues such as frozen sections taken for histological purposes.

A "chronic illness" is a disease, symptom, or syndrome that last for months to years. Examples of chronic illnesses include cancers (e.g., multiple myeloma, leukemia, breast cancer, ovarian cancer, head and neck cancer, brain cancer, cervical cancer, testicular cancer, prostate cancer, Hodgkins Disease, and the like), precancerous conditions ( e.g., adenomatous polyposis coli (APC)), chronic fatigue syndrome, autoimmune diseases (e.g., arthritis, multiple sclerosis, lupus, scleroderma, and the like) diabetes, asthma, heart disease, neuromuscular diseases (e.g., fibromyalgia), neurodegenerative diseases (e.g., ALS, Alzheimer's Disease, and Parkinson's Disease), AIDS, Persian Gulf War Related Illnesses and chronic hepatitis.

A "fragile site" is a locus within the human genome that is a frequent site of DNA strand breakage. Fragile sites are typically identified cytogenetically as gaps or discontinuities as a result of poor staining. Fragile sites are classified as common or rare and further divided according to the agents used to induce them. For a general description of fragile sites and their classification, see, Sutherland *GATA* 8:1961–166 (1991). Exemplified sequences disclosed here include sequences from viral genomes that have apparently been inserted into the human genome at a fragile site. Thus, fragile sites can contain "archived nucleic acid sequences" which result from a wide range of pathogens, including bacteria, parasites, and viruses.

A "target human nucleic acid" of the invention is a nucleic acid molecule derived from human genomic DNA (e.g., chromosomal DNA, mitochondrial DNA, and other extra-chromosomal DNA). As used herein human genomic DNA refers to germline DNA and may also include nucleic acids introduced into the individual as a result of infection of the individual by a pathogenic microorganism (e.g., exogenous viral DNA integrated into the genome after infection or through live virus infection). Thus, although target human nucleic acids of the invention are of human origin, they may nonetheless contain sequences shared by other pathogenic organisms, such as viruses. Such sequences are sometimes referred to here as human/viral chimeric sequences or "archived sequences". DNA "derived from" human genome DNA includes DNA molecules consisting of subsequences of the genomic DNA as well as RNA molecules transcribed from human genomic DNA.

The RNA molecules detected in the methods of the invention may be free, single or double stranded, molecules or complexed with protein. Such RNA molecules need not be transcribed from a gene, but can be transcribed from any sequence in the chromosomal DNA. Exemplary RNAs include small nuclear RNA (snRNA), mRNA, tRNA, and rRNA.

The terms "hybridize(s) specifically" or "specifically hybridize(s)" refer to complementary hybridization between an oligonucleotide (e.g., a primer or labeled probe) and a target sequence. The term specifically embraces minor mismatches that can be accommodated by reducing the stringency of the hybridization media to achieve the desired priming for the PCR polymerases or detection of hybridization signal.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

The term "oligonucleotide" refers to a molecule comprised of two or more deoxyribonucleotides or ribonucleotides, such as primers, probes, nucleic acid fragments to be detected, and nucleic acid controls. The exact size of an oligonucleotide depends on many factors and the ultimate function or use of the oligonucleotide.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide sequence. The appropriate length of a primer depends on the intended use of the primer but typically ranges from about 15 to about 30 nucleotides. Short primer molecules generally require cooler temperatures to form sufficiently stable hybrid complexes with the template. A primer need not reflect the exact sequence of the template but must be sufficiently complementary to specifically hybridize with a template.

"Probe" refers to an oligonucleotide which binds through complementary base pairing to a subsequence of a target nucleic acid. It will be understood by one of skill in the art that probes will typically substantially bind target sequences lacking complete complementarity with the probe sequence depending upon the stringency of the hybridization conditions. The probes are typically directly labeled (e.g., with isotopes or fluorescent moieties) or indirectly labeled such as with digoxigenin or biotin. By assaying for the presence or absence of the probe, one can detect the presence or absence of the target.

The term "regulatory sequence" refer to cis-acting sequences (either 5' or 3') necessary for efficient transcription of structural sequences (e.g., open reading frames). These sequences include promoters, enhancers and other sequences important for efficient transcription and translation (e.g., polyadenylation sites, mRNA stability controlling sequences and the like).

A "sequence specific to" a particular virus species or strain (e.g., poliovirus) is a sequence unique to the species or strain, that is, not shared by other previously characterized species or strains. A probe or primer containing a sequence complementary to a sequence specific to a virus will typically not hybridize to the corresponding portion of the genome of other viruses under stringent conditions (e.g., washing the solid support in 2×SSC, 0.1% SDS at about 60° C., preferably 65° C. and more preferably about 70° C.).

The term "substantially identical" indicates that two or more nucleotide sequences share a majority of their sequence. Generally, this will be at least about 90% of their sequence and preferably about 95% of their sequence. Another indication that sequences are substantially identical is if they hybridize to the same nucleotide sequence under stringent conditions (see, e.g., Sambrook et al., *Molecular Cloning—A Laboratory Manual*, Cold Spring Harbor Laboratory, Cold Spring Harbor, N.Y., 1985). Stringent conditions are sequence-dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 60° C. For example, a nucleic acid of the invention or fragment thereof can be identified in standard filter hybridizations using the nucleic acids disclosed here under stringent conditions, which for purposes of this disclosure, include at least one wash (usually 2) in 0.2×SSC at a temperature of at least about 60° C., usually about 65° C., sometimes 70° C. for 20 minutes, or equivalent conditions.

As used herein a "viral nucleic acid" is a nucleic acid molecule comprising nucleic acid sequences derived from viruses. Since as described below, the viral nucleic acids disclosed here are thought to be derived from recombination events, the viral nucleic acids of the invention may contain sequences derived from other microorganisms or from cellular sequences.

A nucleic acid comprising a "complete viral genome" is a nucleic acid molecule encoding all the polypeptide products required to construct a complete, infectious viral particle. For instance, in the case of enteroviruses, a complete viral genome would be a nucleic acid encoding all the protein products identified in FIG. 1. As used herein a complete, infectious viral particle can be encoded by a sequence that is a full length genome, as well as a substantially full length (e.g., 90%, preferably 95% complete) genome.

DESCRIPTION OF THE PREFERRED EMBODIMENT

Figure 1:
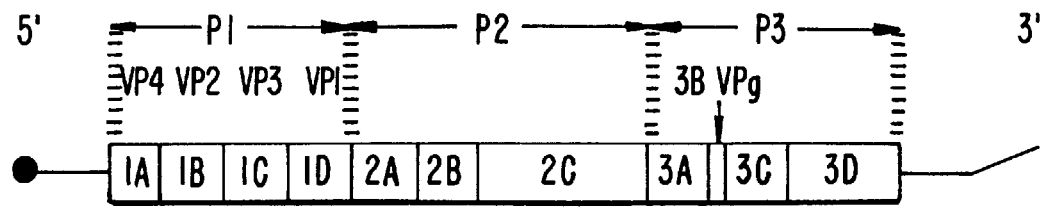
FIG. 1 shows the genome structure and gene organization of enteroviruses. The filled circle at the 5' end is the genome-linked protein VPg (also referred to as the 3B gene product), followed by, the 5' non-translated region (5' NTR; solid line). The open box depicts the long ORF encoding the polyprotein that is followed by the 3' non-translated region (line) and a poly (A) track (angled line). The eventual cleavage products of the polyprotein are indicated by vertical lines in the boxes. The P1 region encodes the structural proteins 1A, 1B, 1C and 1D, usually referred to as VP4, VP2, VP3, and VP1, respectively.

The present invention is based in part on the surprising discovery of novel human and archived nucleic acids in biological fluids. The detection of these previously undetected human nucleic acids is useful in the early diagnosis and continuous monitoring of diseases, particularly chronic illnesses. In addition, targetted destruction of cells from which these nucleic acids are being lost can be used to treat these diseases. The detection methods of the invention can also be used to monitor the success of treatment of disease.

In some embodiments of the invention the target sequences are sequences found in chromosomal fragile sites. Without wishing to be bound by theory, it is believed that nucleic acids in particular chromosomal regions (e.g., fragile sites) are preferentially released from diseased or damaged cells early in or during the disease process. The nucleic acids can be released as a result of a number of events including contact with agents that create damage to cells, particular genetic material (genotoxic agents). Such events include integration and/or expression of viral DNA or retroelements, and contact with genotoxic agents such as aflatoxins, organophosphate poisons (e.g., pesticides and nerve gas agents, nitrogen mustards), other chemical warfare agents, benzene, cigarette carcinogens, digoxins, dioxin, biotoxins, UV light, radioactive particles, and other cell damaging radiation exposures.

Repetitive DNA sequences are commonly associated with fragile sites. Thus, in some embodiments of the invention; repetitive sequences are detected in the invention. Exemplary repetitive sequences include Alu and Kpn families of repetitive DNA. Repetitive sequences can also be categorized into long interspersed elements (LINEs) and short interspersed elements (SINEs) (see, Wilkinson et al. in *The Retroviridae* Vol. 3, J. A. Levy (ed.), pp 465–535, Plenum Press, New York (1994)). Kpn elements are examples of LINEs, where as Alu elements are examples of SINEs. LINEs, unlike SINEs, contain open reading frames encoding proteins with reverse transcriptase activity. Both LINEs and SINEs are examples of retroposons, which are a subcategory of retroelement, that is, a transposable element in the genome that transposes via an RNA intermediate. Retroposons are distinguished from retrotransposons (also referred to as human endogenous retroviruses or HERVs) by the absence of long terminal repeats (LTRs). The relationship between HERVs and various disease states as well as diagnostic detection of antibodies to HERV antigens is discussed in WO 95/32311.

In some embodiments of the invention, Alu sequences or elements are detected in the methods of the invention. Alu elements are present in 105 to 106 copies in the human genome. Each element is about 300 base pairs in length and includes a polyA tract at the 3' end. It is thought that the sequences are derived from a gene encoding the 7SL structural RNA, which is a component of the signal recognition particle located on the rough endoplasmic reticulum.

In some preferred embodiments, RNA molecules derived from Alu sequences from fragile sites are detected. In the example provided below, Alu sequences from a fragile site on the long arm of chromosome 22 (22q12-13) are detected. As shown below, detection of these sequences is associated with multiple myeloma. Translocations and other abnormalities have been associated this region with a number of diseases including schizophrenia (see, e.g., Kalsi et al. *Am. J. Med. Genet.* 60:298–301 (1995)) and cancers (see, e.g., Stenman et al., *Int. J. Cancer* 62:398–402 (1995)).

As noted above, fragile sites may contain repeated sequences. Repeated sequences are known to contain sequences that bind nuclear proteins and are effective in regulating gene expression. Evidence indicates that mobile elements such as segments of repetitive DNA (e.g., LTRs from retroviruses and Alu sequences) have inserted in various sites in the genome and have affected regulation of gene expression (see, e.g., Britten et al. *Proc. Nat. Acad. Sci. USA* 93:9374–9377 (1996). Without wishing to be bound by theory it is believed that alteration of these sequences by insertion of retroelements or genotoxic agents may lead to altered expression of sequences within the genome.

The nucleic acids detected in the methods of the invention are typically from about 100 nucleotides to several thousand nucleotides in length. Usually, the nucleic acids are from about 200 to about 1500 nucleotides.

The present invention is also directed to the detection of non-poliovirus nucleic acids (NPVNA) and recombinants between polio and other viruses. In some embodiments that non-polioviruses are other members of the picornaviridae, such as non-polioenteroviruses (NPEV). In particular, the invention provides sensitive methods (e.g., the polymerase chain reaction, PCR) for detecting NPVNA and recombinant viruses potentially derived from polio vaccines.

A schematic diagram of an enterovirus genome is provided in FIG. 1. Enteroviruses contain one molecule of infectious, positive sense, ssRNA, typically between about 7 and about 8.5 kb in size. The genome comprises a 5' nontranslated region (5' NTR) of variable length followed by an ORF encoding the polyprotein precursor (240–250 Kd) to the structural proteins (P1) and the predominantly nonstructural proteins (P2, P3), followed by a short non-coding sequence and a poly (A) tract of variable length. Virion proteins include 60 copies each of the four capsid proteins, which are gene products of the P1 region (IA, IB, IC, ID), which are also referred to as VP4, VP2, VP3, VP1, respectively.

The complete nucleotide sequences of various enteroviruses are available in the scientific literature and in databases such as GenBank. Using this information, one of skill can design appropriate primers and probes targeting desired regions of the NPV or poliovirus genome. For instance, sequences of poliovirus types 1, 2 and 3 are available from GenBank Accession Numbers POLIOS1 (Sabin strain 1), PIPOLS2 (Sabin strain 2), POL3L12CG (Sabin strain 3). The sequences are also disclosed in Toyoda et al., *J. Mol Biol* 174: 561–585, (1984).

The present invention is based in part on the surprising discovery of contaminating NPVNA in poliovirus vaccine preparations. The detection of these previously undetected viral components is clearly important to maintaining safe effective vaccines for poliomyelitis. In addition, the invention provides evidence suggesting that attenuated polioviruses in vaccine preparations may recombine with NPVNA present in the host gut or in the vaccine to produce new and potentially pathogenic viruses. Evidence provided below suggests the presence of such recombinants in Gulf War veterans diagnosed with Gulf War Syndrome. The occurrence of these recombinants is also detected in patients diagnosed with other diseases. Examples include multiple myeloma, prostate cancer, Parkinson's Disease, multiple sclerosis, and the like.

Selection of the primers used in the invention is based on what target sequences are being detected. In the case where contaminating NPEV are being detected (e.g., in a poliovirus vaccine preparation) primers which specifically hybridize to any region of the enterovirus genome can be used. Typically, primers specific for conserved regions in the enterovirus genome are used. Examples of suitable target sequences are those present in the 5' nontranslated region of the genome. Exemplary primers for this purpose include primers which hybridize to nucleotides 163–178 or 443–460 of the poliovirus genome.

If NPV-poliovirus recombinants are being detected, a primer specific for poliovirus sequences is used in combination with a primer which hybridizes to sequences conserved in a picornaviral genome, for example an enteroviral genome. Polio-specific primers will typically hybridize to the genes encoding the polyprotein precursors P1, P2, and P3 in the poliovirus genome. Exemplary primers are those that hybridize to nucleotides 4460–4478, 4634–4653, 4922–4941, or 5467–5487 of the poliovirus genome.

The diagnostic methods of the invention typically rely on a method of amplifying the target nucleic acid from a biological fluid (e.g., serum or plasma). PCR amplification of the target nucleic acid is typically used. One of skill will recognize, however, that amplification of target sequences in a sample may be accomplished by any known method, such as ligase chain reaction (LCR), QP-replicase amplification, transcription amplification, and self-sustained sequence replication, each of which provides sufficient amplification.

The PCR process is well known in the art and is thus not described in detail herein. For a review of PCR methods and protocols, see, e.g., Innis, et al. eds. *PCR Protocols. A Guide to Methods and Application* (Academic Press, Inc., San Diego, Calif. 1990). PCR reagents and protocols are also available from commercial vendors, such as Roche Molecular Systems.

In some embodiments of the invention, RNA molecules may be detected (e.g., detection of enteroviral sequences). The detected RNA molecules may be also be RNA transcribed from genomic sequences, but which do not encode functional polypeptides. The first step in the amplification is the synthesis of a DNA copy (cDNA) of the region to be amplified. Reverse transcription can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described in Romero and Rotbart in *Diagnostic Molecular Biology: Principles and Applications* pp.401–406, Persing et al. eds., (Mayo Foundation, Rochester, Minn. 1993); Rotbart et al. U.S. Pat. No. 5,075,212 and Egger et al., *J. Clin. Microbiol.* 33:1442–1447 (1995)).

The primers used in the methods of the invention are preferably at least about 15 nucleotides to about 50 nucleotides in length, more preferably from about 15 nucleotides to about 30 nucleotides in length.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids, in particular ribonucleic acids, from biological samples are known in the art. As noted above, the samples of the invention are acellular biological fluids.

The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In the preferred embodiment of the PCR process, strand separation is achieved by heating the reaction to a sufficiently high temperature for an sufficient time to cause the denaturation of the duplex but not to cause an irreversible denaturation of the polymerase (see U.S. Pat. No. 4,965,188). Template-dependent extension of primers in PCR is catalyzed by a polymerizing agent in the presence of adequate amounts of four deoxyribonucleoside triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis. In the present invention, the initial template for primer extension is typically RNA. Reverse transcriptases (RTs) suitable for synthesizing a cDNA from the RNA template are well known.

PCR is most usually carried out as an automated process with a thermostable enzyme. In this process, the temperature of the reaction mixture is cycled through a denaturing region, a primer annealing region, and an extension reaction region automatically. Machine specifically adapted for this purpose are commercially available from Roche Molecular Systems.

The target human nucleic acids of the invention can also be detected using other standard techniques, well known to those of skill in the art. Although the detection step is typically preceded by an amplification step, amplification is not required in the methods of the invention. For instance, the nucleic acids can be identified by size fractionation (e.g., gel electrophoresis). The presence of different or additional bands in the sample as compared to the control, is an indication of the presence of target nucleic acids of the invention. Alternatively, the target nucleic acids can be identified by sequencing according to well known techniques. Alternatively, oligonucleotide probes specific to the target nucleic acids can be used to detect the presence of specific fragments.

As explained in detail below, the size of the amplified fragments produced by the methods of the invention is typically sufficient to distinguish polioviruses from either NPV or poliovirus recombinants. Thus, in some embodiments of the invention, size fractionation (e.g., gel electrophoresis) of the amplified fragments produced in a given sample can be used to distinguish poliovirus from other viruses of interest. This is typically carried out by amplifying a control containing known viruses (e.g., isolated poliovirus) with the same primers used to amplify the sample of interest. After running the amplified sequences out in an agarose or polyacrylamide gel and labeling with ethidium bromide according to well known techniques (see, Sambrook et al.), the pattern of bands in the sample and control are compared. The presence of different or additional bands in the sample as compared to the control, is an indication of the presence of NPV or poliovirus recombinants.

Sequence-specific probe hybridization is a well known method of detecting desired nucleic acids in a sample comprising cells, biological fluid and the like. Under sufficiently stringent hybridization conditions, the probes hybridize specifically only to substantially complementary sequences. The stringency of the hybridization conditions can be relaxed to tolerate varying amounts of sequence mismatch. If the target is first amplified, detection of the amplified product utilizes this sequence-specific hybridization to insure detection of only the correct amplified target, thereby decreasing the chance of a false positive caused by the presence of homologous sequences from related organisms or other contaminating sequences.

A number of hybridization formats well known in the art, including but not limited to, solution phase, solid phase, mixed phase, or in situ hybridization assays. In solution (or liquid) phase hybridizations, both the target nucleic acid and the probe or primer are free to interact in the reaction mixture. In solid phase hybridization assays, either the target or probes are linked to a solid support where they are available for hybridization with complementary nucleic acids in solution. Exemplary solid phase formats include Southern hybridizations, dot blots, and the like. In situ techniques are particularly useful for detecting target nucleic acids in chromosomal material (e.g., in metaphase or interphase cells). The following articles provide an overview of the various hybridization assay formats: Singer et al., *Biotechniques* 4:230 (1986); Haase et aL, METHODS IN VIROLOGY, Vol. VII, pp. 189–226 (1984); Wilkinson, IN SITU HYBRIDIZATION, D. G. Wilkinson ed., IRL Press, Oxford University Press, Oxford; and NUCLEIC ACID HYBRIDIZATION: A PRACTICAL APPROACH, Hames, B. D. and Higgins, S. J., eds., IRL Press (1987).

The hybridization complexes are detected according to well known techniques and is not a critical aspect of the present invention. Nucleic acid probes capable of specifically hybridizing to a target can be labeled by any one of several methods typically used to detect the presence of hybridized nucleic acids. One common method of detection is the use of autoradiography using probes labeled with 3H, 125I, 35S, 14C, or 32P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers of the invention can be synthesized and labeled using well known techniques. Oligonucleotides for use as probes and primers may be chemically synthesized according to the solid phase phosphoramidite triester method first described by Beaucage, S. L. and Caruthers, M. H., 1981, Tetrahedron Letts., 22(20): 1859–1862 using an automated synthesizer, as described in Needham-VanDevanter, D. R., et al. 1984, Nucleic Acids Res., 12:6159–6168. Purification of oligonucleotides is by either native acrylamide gel electrophoresis or by anion-exchange HPLC as described in Pearson, J. D. and Regnier, F. E., 1983, J. Chrom., 255:137–149.

The present invention also provide kits, multicontainer units comprising components useful for practicing the present method. A useful kit can contain probes for detecting the desired target nucleic acid, from either a recombinant virus or an NPV. In some cases, the probes may be fixed to an appropriate support membrane. The kit will also contain primers for RT-PCR. Other optional components of the kit include, for example, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. In addition to the above components, the kit can also contain instructions for carrying out the present method.

The invention provides methods of treating chronic illnesses. Generally, the therapeutic methods rely on therapies designed to significantly reduce the presence of acellular nucleic acids or to selectively destroy cells from which nucleic acids are being lost. In many cases, such cells are dysplastic, particularly in the case of cancers. Thus, compounds that can selectively destroy such Cells can be used to inhibit the disease process. For instance, compounds that selectively induce apoptosis in target dysplastic or neoplastic cells can be used in this approach. Example of such compounds are sulindac-derived compounds such as sulindac sulfone, a non-steroidal anti-inflammatory drug. Sulindac, is a widely used arthritis drug and anti inflammatory agent which reduces the growth of colon polyps in patients with adenomatous polyposis coli (APC). The growth inhibitory effect of sulindac sulfone results from the ability of that compound to selectively augment cell death through apoptosis, rather than by arresting the cell cycle.

Any number of anti-neoplastic compounds and therapies known to those skilled in the art can be used in the present invention. Such compounds work by a number of mechanisms including inhibition of purine or pyrimidine synthesis, inhibition of deoxyribonucleotide synthesis, cross-linkage of DNA, inhibition of microtubuke formation and the like. For a description of a variety of chemotherapeutic agents, see, *Principles of Internal Medicine* 12th ed. pp 1587–1599 Wilson el al. (eds.), McGraw-Hill, Inc. 1991)

Suitable pharmaceutical formulations for use in the present invention are found in *Remington's Pharmaceutical Sciences*, Mack Publishing Company, Philadelphia, Pa., 17th ed. (1985). A variety of pharmaceutical compositions comprising compounds and pharmaceutically acceptable carriers can be prepared.

Injectable preparations, for example, sterile injectable aqueous suspensions may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The pharmaceutical compositions containing the compounds can be administered for therapeutic treatments. In therapeutic applications, compositions are administered to a patient already suffering from a disease, as described above, in an amount sufficient to decrease and preferably cure or at least partially arrest the symptoms of the disease and its complications. An amount adequate to accomplish this is defined as "therapeutically effective dose." Amounts effective for this use will depend on the compound being administered, the severity of the disease, the weight and general state of the patient and the judgement of the prescribing physician.

EXAMPLES

Example 1

The following example provides the results of PCR studies of samples derived from Gulf War Veterans diagnosed with Gulf War Syndrome. The PCR conditions were generally those described in Egger et al., *J. Clin. Microbiol.* 33:1442–1447 (1995)). The primers used in the assays are summarized in Table 1, below. Table 1 also provides information about the map position, expected product and specificity of each primer. The 5' to 3' sequence of the primers used is as follows:

PG01 AAGCACTTCTGTTTCC (SEQ. ID. NO:1)
PG02 CATTCAGGGGCCGGAGGA (SEQ. ID. NO:2)
PG03 GAATGTGTAAGAACTGTCA (SEQ ID NO:3)
PG04 GTAAACAATGTTTCTTTTAGCC (SEQ ID NO:4)
PG07 CAGTTCAAGAGCAA(A/G)CACC (SEQ ID NO:5)
PG08 TC(A/G)TCCAT(A/G)AT(A/C)AC(T/C)AC(T/A)CC (SEQ ID NO:6)

Briefly, the amplifications were carried out used as follows. RNA from 0.25 ml of the sample (serum or plasma, preferably non-heparinized) was extracted using 0.75 ml of TRIZOL LS reagent (Gibco BRL, Gaithersburg, Md.), and the RNA was precipitated with 10 µg of Rnase-free glycogen as a carrier. Both methods were performed according to the protocols of the manufacturer.

The precipitated RNA was washed once with 70% ethanol by centrifugation at 4° C., resuspended in 10 µl of Rnase-free distilled water, and added to 17 µl of the RT mixture (GeneAmp RNA PCR kit; Perkin-Elmer, Norwalk, Conn.) containing MgCl₂(5 mM), 1×PCR Buffer II, Rnase Inhibitor (2.5 U), MuLV Reverse Transcriptase (2.5 U), random hexamer primers (2.5 µM), and 1 mM each of dATP, dGTP, dCTP and dTTP. The mixture was incubated for 10 minutes at 22° C., 30 minutes at 42° C., 5 minutes at 95° C. using a Perkin-Elmer Thermocycler. The RT mixture was then added to the top PCR mixture of a Hot Start PCR reaction using a melted Ampliwax bead (Perkin-Elmer, Norwalk, Conn.) as the barrier. The 70 µl top PCR mixture contains 1×PCR Buffer II and Amplitaq (2.5 U). The 30 µl bottom PCR mixture contains 1×PCR Buffer II, 2 mM MgCl₂, and the appropriate primer pairs (15 µM). After 35 cycles (1 min at 94° C., 2 min at 48° C., and 1 min at 72° C.), 8 µl of the PCR mixture was subjected to electrophoresis using a Pre-Cast 4–20% gradient or a 6% polyacrylamide gel in TBE Buffer (45 mM boric acid, 1 mM EDTA) (NOVEX, San Diego, Calif.) for 45 minutes and 60 minutes, respectively, at 200 volts. After electrophoresis, the gel was stained in a 0.5 µg/ml solution of ethidium bromide solution for 20 minutes and the bands were photographed under UV light.

TABLE 1

PRIMER SUMMARY

| PRIMER | PRIMER REGION (Sabin genome) | MAP POSITION (NUCLE-OTIDE #) | PRIMER LENGTH (# of bases) | EXPECTED PRODUCT LENGTH (base pairs) | SPE-CIF-ICITY |
|---|---|---|---|---|---|
| PG01 | 5'NTR | 163–178 | 16 | 297 (about 300) if combined with PG02 | Picorna-virus |
| PG02 | 5'NTR | 443–460 | 18 | 297 (about 300) when combined with PG01 | Picorna-virus |
| PG03 | P2–P3 REGION | 4922–4941 | 20 | 565 when combined with PG04 | Polio Type 1 & 2 |
| PG04 | P2–P3 REGION | 5467–5487 | 21 | 565 when combined with PG03 | Polio Type 1 & 2 |
| PG07 | P2 REGION | 4460–4478 | 19 | 193 (about 200) when combined with PG08 | Polio Type 1, 2 & 3 |
| PG08 | P2 REGION | 4634–4653 | 20 | 193 (about 200) when combined with PG07 | Polio Type 1, 2 & 3 |

NOTE:
PG04 & PG07 primer combination can produce a 1000 base pair PCR product

As can be seen in Table 2, the amplification using these primers led to a number of unexpected products. For instance, in the trivalent, oral polio vaccine (OPV) preparation (column 2), amplification using PG01 and PG02 (both specific to the 5' NTR) was expected to produce fragments of about 300 bp. Instead, a series of additional, unexpected products ranging in length from about 310 to about 460 bp were observed (lengths reported in Table 2 are lengths as determined by gel electrophoresis). Similar results were found when PG07 and PG08 were used. This result was not seen in the inactivated polio vaccine (IPV) grown in human cells. The presence of these additional fragments are strong evidence that other contaminating viruses are present in the vaccine.

One amplified fragment of about 360 base pairs generated using PG01 and PG02 was sequenced (SEQ ID NO:7). Sequence analysis revealed that the fragment may have arisen due to an inverted repeat with sequences from Sabin strain 1 and Sabin strain 2. A second fragment generated by these primers was also sequenced from four different clones (SEQ ID NOS:8–11).

In addition, serum samples from Gulf War Veterans diagnosed with Persian Gulf War Related Illness (PGWRI) from one VA hospital showed unexpected bands using primers specific to the 5'NTR (Table 2, column 4). When these primers were used in combination with primers specific to poliovirus sequences a number of unexpected fragments were also seen. A control group of insurance applicants (Table 2, column 5) had a much lower occurrence and number of unexpected fragments. The occurrence of some unexpected fragments in this group indicates that some recombinants may also occur in this group, as well.

A particular 400 bp fragment, amplified by primers PG02 and PG03 was seen in 3 out of 3 serum samples from Gulf War veterans at the VA hospital in Martinez, Calif. This fragment was isolated and sequenced (SEQ ID NOS:12–16)). The sequences in these samples showed no significant sequence identity with any known sequence. A second fragment of about 1200 basepairs was also sequenced (SEQ ID NO:17). A third fragment of about 750 basepairs was also found and sequenced from three different veterans (SEQ ID NOS:18–20). Two other fragments have also been sequenced (SEQ ID NOS:21 and 22). These results suggest that the amplified fragment contains sequences from an uncharacterized virus.

Unexpected bands have been observed in patients diagnosed with other diseases. For example, Table 2 shows results from patients with multiple sclerosis (MS) and prostate cancer.

TABLE 2

PRODUCT LENGTHS in base pairs (# of positive samples/total samples screened)

| PRIMER PAIR | SABIN I LAB CONTROL 1 lot | OPV 5 lots | IPV 1 lot | VA | | OSBORN INSURANCE | | MS | | PROSTATE CANCER | | MULTIPLE MYELOMA | |
|---|---|---|---|---|---|---|---|---|---|---|---|---|---|
| PG01/PG02 | | | | | | | | | | | | | |
| EXPECTED: | 300 | 300 | 300 | NONE | | NONE | | NOT DONE | | NOT DONE | | NOT DONE | |
| OTHER: | NONE | ~310 | | 760 | (3/3) | 200 | (9/10) | | | | | | |
| | | 357 | | 1200 | (3/3) | 290 | (2/10) | | | | | | |
| | | ~380 | | | | | | | | | | | |
| | | ~410 | | | | | | | | | | | |
| | | 463 | | | | | | | | | | | |
| PG03/PG04 | | | | | | | | | | | | | |
| EXPECTED: | 565 | 565 | NOT DONE | NONE | | NOT DONE | | NOT DONE | | NOT DONE | | NOT DONE | |
| OTHER: | NONE | NONE | | 647 | (1/3) | | | | | | | | |
| | | | | 540 | (3/3) | | | | | | | | |
| | | | | ~600 | (1/3) | | | | | | | | |
| | | | | ~1500 | (2/3) | | | | | | | | |
| PG07/PG08 | | | | | | | | | | | | | |
| EXPECTED: | 200 | 200 | 200 | NONE | | NOT DONE | | NOT DONE | | NOT DONE | | NOT DONE | |
| OTHER | NONE | 210 | NONE | 200 | (2/2) | | | | | | | | |
| | | 290 | | 750 | (2/2) | | | | | | | | |
| | | | | 750 | (1/2) | | | | | | | | |
| | | | | 1500 | (2/2) | | | | | | | | |
| PG02/PG03 | | | | | | | | | | | | | |
| EXPECTED: | NONE | NONE | NOT DONE | NONE | | NOT DONE | | NOT DONE | | NOT DONE | | NOT DONE | |
| OTHER: | NONE | NONE | | 414 | (3/3) | | | | | | | | |
| PG01/PG02/ PG03/PG04 | | | | | | | | | | | | | |
| EXPECTED: | 300 | 300 | NOT DONE | NONE | | NONE | | 300 | | NONE | | NONE | |
| | 565 | 565 | | | | | | | | | | | |
| OTHER: | NONE | 310 | | 300 | (7/23) | 200 | (17/22) | 210 | (1/1) | 100 | (2/2) | 200 | (1/1) |
| | | 350 | | 310 | (1/23) | 290 | (13/22) | | | 200 | (2/2) | 350 | (1/1) |
| | | 380 | | 400 | (12/23) | 350 | (1/22) | | | 300 | (2/2) | 380 | (1/1) |
| | | 410 | | 565 | (7/23) | 310 | (8/22) | | | 310 | (2/2) | 400 | (1/1) |
| | | 460 | | 750 | (4/23) | | | | | 350 | (2/2) | 450 | (1/1) |
| | | | | 1200 | (9/23) | | | | | 400 | (2/2) | 500 | (1/1) |
| | | | | | | | | | | 650 | (2/2) | 800 | (1/1) |
| | | | | | | | | | | 750 | (2/2) | 300 | (1/1) |
| | | | | | | | | | | | | 560 | (1/1) |
| PG01/PG02/ PG07/PG08 | | | | | | | | | | | | | |
| EXPECTED: | 200 | NOT DONE | NOT DONE | NONE | | NOT DONE | | NOT DONE | | NOT DONE | | NOT DONE | |
| | 300 | | | | | | | | | | | | |
| | 1000 | | | | | | | | | | | | |
| OTHER: | NONE | NOT DONE | | 190 | (1/1) | | | | | | | | |
| | | | | 210 | (1/1) | | | | | | | | |
| | | | | 310 | (1/1) | | | | | | | | |
| | | | | 410 | (1/1) | | | | | | | | |
| | | | | 580 | (1/1) | | | | | | | | |
| | | | | 600 | (1/1) | | | | | | | | |
| | | | | 750 | (1/1) | | | | | | | | |
| | | | | 900 | (1/1) | | | | | | | | |
| | | | | 1500 | (1/1) | | | | | | | | |

TABLE 2-continued

PRODUCT LENGTHS in base pairs (# of positive samples/total samples screened)

| PRIMER PAIR | SABIN I LAB CONTROL 1 lot | OPV 5 lots | IPV 1 lot | VA | | OSBORN INSURANCE | MS | PROSTATE CANCER | MULTIPLE MYELOMA |
|---|---|---|---|---|---|---|---|---|---|
| PG03/PG04/ PG07/PG08 | | | | | | | | | |
| EXPECTED: | 200 565 | NOT DONE | NOT DONE | NONE | | NOT DONE | NOT DONE | NOT DONE | NOT DONE |
| OTHER: | NONE | NOT DONE | | 190 | (1/1) | | | | |
| | | | | 210 | (1/1) | | | | |
| | | | | 310 | (1/1) | | | | |
| | | | | 410 | (1/1) | | | | |
| | | | | 250 | (1/1) | | | | |
| | | | | 550 | (1/1) | | | | |
| | | | | 580 | (1/1) | | | | |
| | | | | 750 | (1/1) | | | | |
| | | | | 1500 | (1/1) | | | | |
| PG01/PG02/ PG03/PG04/ PG07/PG08 | | | | | | | | | |
| EXPECTED: | 200 300 565 (1000) | 200 300 565 | 200 300 565 | ? | | NOT DONE | NOT DONE | NOT DONE | NOT DONE |
| OTHER: | NONE | 310 (5/5) | NONE | 190 | (1/1) | | | | |
| | | 350 (5/5) | | 250 | (1/1) | | | | |
| | | 380 (5/5) | | 310 | (1/1) | | | | |
| | | 410 (5/5) | | 450 | (1/1) | | | | |
| | | 46 (5/5) | | 540 | (1/1) | | | | |
| | | 700 (5/5) | | 580 | (1/1) | | | | |
| | | | | 750 | (1/1) | | | | |
| | | | | 900 | (1/1) | | | | |
| | | | | 1500 | (1/1) | | | | |

Example 2

The following example provides the results of PCR studies of plasma samples derived from multiple myeloma patients. The primers used in the present studies were designed to amplify enteroviral sequence and were based on sequences of the enteroviral genome (Egger et al., *J. Clin. Microbiol.* 33:1442–1447 (1995)).

Materials and Methods

The primers used in the assays are summarized below.
PG01 AAGCACTTCTGTTTCC (SEQ ID NO:1)
PG02 CATTCAGGGGCCGGAGGA (SEQ ID NO:2)

The amplifications were carried out generally described above.

Results

Amplification of nucleic acids in serum samples from four multiple myeloma patients produced the same amplicon of approximately 700 base pairs (SEQ ID NOs: 23–26). These sequences includes Alu sequences found at 22q12. The presence of the same nucleic acid in three different patients in different parts of the country is an indication that the detection of these sequences is important in the detection of myeloma and other diseases.

Figure 2:
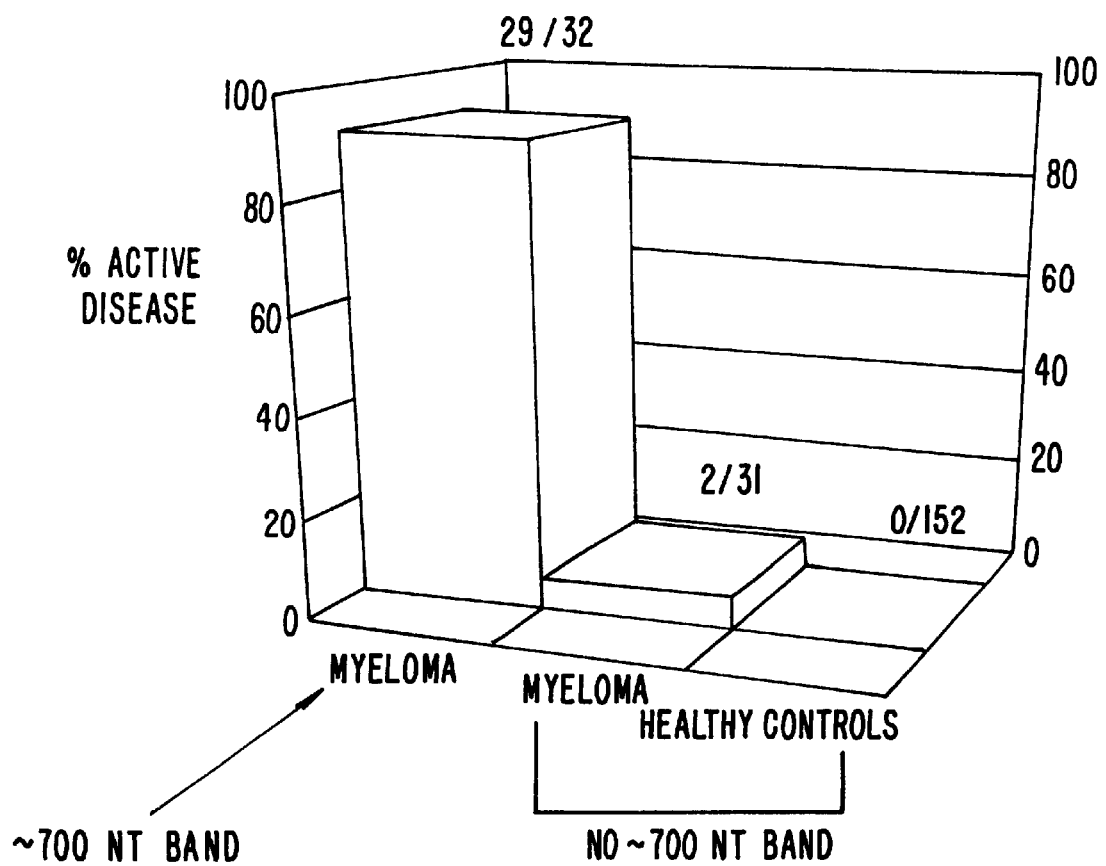
FIG. 2 is a bar graph showing the percentages of myeloma patients with active disease (either with or without the 700 nt band).

In addition, the same size band has been detected in 32 myeloma patients, 29 of whom had active disease. The band was not detected in an additional 31 myeloma patients, only 2 of whom had active disease. Finally, the band was not detected in 152 healthy controls. The results are presented graphically in FIG. 2.

Example 3

As noted above, the sequences detected in myeloma patients were amplified using primers based on sequences in the enteroviral genome.

Amplifications using the primers of Example 1 were carried out as described above. The results are presented in Table 3. As can be seen in Table 3, the amplification using these primers led to a number of unexpected products.

TABLE 3

PRODUCT LENGTHS in base pairs (# of positive samples/total samples screened)

| PRIMER PAIR | VA | | OSBORN INSURANCE | | MS | PROSTATE CANCER | MULTIPLE MYELOMA |
|---|---|---|---|---|---|---|---|
| PG01/PG02 | | | | | | | |
| EXPECTED: | NONE | | NONE | | NOT DONE | NOT DONE | NOT DONE |
| OTHER: | 760 | (3/3) | 200 | (9/10) | | | |
| | 1200 | (3/3) | 290 | (2/10) | | | |

TABLE 3-continued

PRODUCT LENGTHS in base pairs (# of positive samples/total samples screened)

| PRIMER PAIR | VA | OSBORN INSURANCE | MS | PROSTATE CANCER | MULTIPLE MYELOMA |
|---|---|---|---|---|---|
| PG03/PG04 | | | | | |
| EXPECTED: | NONE | NOT DONE | NOT DONE | NOT DONE | NOT DONE |
| OTHER: | 647 (1/3) | | | | |
| | 540 (3/3) | | | | |
| | ~600 (1/3) | | | | |
| | ~1500 (2/3) | | | | |
| PG07/PG08 | | | | | |
| EXPECTED: | NONE | NOT DONE | NOT DONE | NOT DONE | NOT DONE |
| OTHER: | 200 (2/2) | | | | |
| | 750 (2/2) | | | | |
| | 750 (1/2) | | | | |
| | 1500 (2/2) | | | | |
| PG02/PG03 | | | | | |
| EXPECTED: | NONE | NOT DONE | NOT DONE | NOT DONE | NOT DONE |
| OTHER: | 414 (3/3) | | | | |
| PG01/PG02/ PG03/PG04 | | | | | |
| EXPECTED: | NONE | NONE | 300 | NONE | NONE |
| OTHER: | 300 (7/23) | 200 (17/22) | 210 (1/1) | 100 (2/2) | 200 (1/1) |
| | 310 (1/23) | 290 (13/22) | | 200 (2/2) | 350 (1/1) |
| | 400 (12/23) | 350 (1/22) | | 300 (2/2) | 380 (1/1) |
| | 565 (7/23) | 310 (8/22) | | 310 (2/2) | 400 (1/1) |
| | 750 (4/23) | | | 350 (2/2) | 450 (1/1) |
| | 1200 (9/23) | | | 400 (2/2) | 500 (1/1) |
| | | | | 650 (2/2) | 800 (1/1) |
| | | | | 750 (2/2) | 300 (1/1) |
| | | | | | 560 (1/1) |
| PG01/PG02/ PG07/PG08 | | | | | |
| EXPECTED: | NONE | NOT DONE | NOT DONE | NOT DONE | NOT DONE |
| OTHER: | 190 (1/1) | | | | |
| | 210 (1/1) | | | | |
| | 310 (1/1) | | | | |
| | 410 (1/1) | | | | |
| | 580 (1/1) | | | | |
| | 600 (1/1) | | | | |
| | 750 (1/1) | | | | |
| | 900 (1/1) | | | | |
| | 1500 (1/1) | | | | |
| PG03/PG04/ PG07/PG08 | | | | | |
| EXPECTED: | NONE | NOT DONE | NOT DONE | NOT DONE | NOT DONE |
| OTHER: | 190 (1/1) | | | | |
| | 210 (1/1) | | | | |
| | 310 (1/1) | | | | |
| | 410 (1/1) | | | | |
| | 250 (1/1) | | | | |
| | 550 (1/1) | | | | |
| | 580 (1/1) | | | | |
| | 750 (1/1) | | | | |
| | 1500 (1/1) | | | | |

TABLE 3-continued

| PRIMER PAIR | VA | | OSBORN INSURANCE | MS | PROSTATE CANCER | MULTIPLE MYELOMA |
|---|---|---|---|---|---|---|
| PG01/PG02/ PG03/PG04/ PG07/PG08 | | | | | | |
| EXPECTED: | ? | | NOT DONE | NOT DONE | NOT DONE | NOT DONE |
| OTHER: | 190 | (1/1) | | | | |
| | 250 | (1/1) | | | | |
| | 310 | (1/1) | | | | |
| | 450 | (1/1) | | | | |
| | 540 | (1/1) | | | | |
| | 580 | (1/1) | | | | |
| | 750 | (1/1) | | | | |
| | 900 | (1/1) | | | | |
| | 1500 | (1/1) | | | | |

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

Table 4 shows SEQ ID NO:7, Table 5 shows SEQ ID NOS:8–11, Table 6 shows SEQ ID NOS:12–16, Table 7 shows SEQ ID NO:17, Table 8 shows SEQ ID NOS:18–20, Table 9 shows SEQ ID NO:21, Table 10 shows SEQ ID NO:22, and Table 1 shows SEQ ID NOS:23–26.

TABLE 4

OPV CLONE #39

(SEQ ID NO:7)

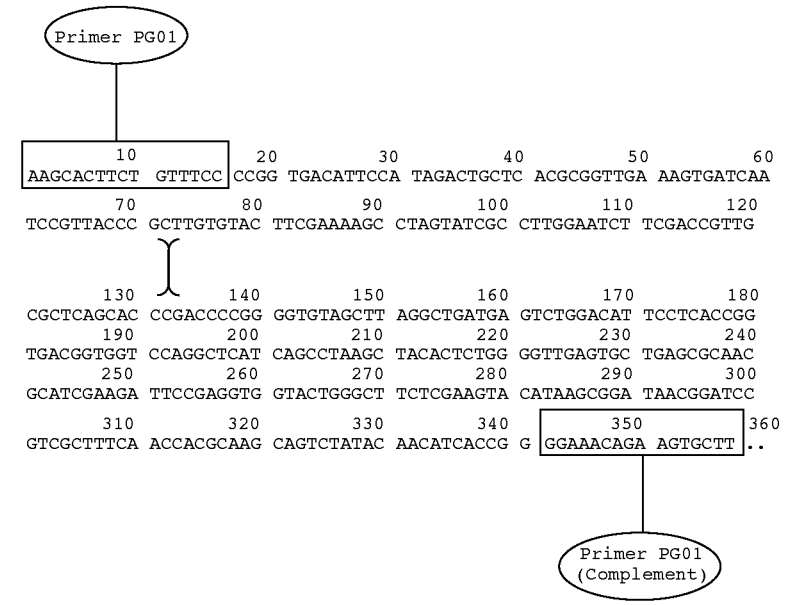

TABLE 5

(SEQ ID NOS: 8–11)

Primer PG01    OPV Clones #42, 43, 45 & 46

```
                       10         20         30         40         50
CLONE #42 --- 1  AAGCACTTCT GTTTCCCACA GATCCTGCAG CACCGTTTGC GTTCCATTAA
CLONE #43 --- 1  AAGCACTTCT GTTTCCCACA GATCCTGCAG CACCGTTTGC GTTC-ATTA-
CLONE #45 --- 1  AAGCACTTCT GTTTCCCAMA GATCCTGCAG CACCGTTTGB GTTCCATTAA
CLONE #46 --- 1  AAGCACTTCT GTTTCCCACA GATCCTGCAG CACCGTTTGC GTTCCATTAA 60         70         80         90        100
             51  CG-CCGCGTT CAAACGTGCG AGGGAATCCT ACGGCTATAA CGGCGATTAC
             51  CG-CCGCGTT CAAACGTGCG AGGGAATCCT ACGGCTATAA CGGCGATTAC
             51  CGSCCGCGTT CAAACGTGCG AGGGAATCCT ACGGCTATAA CGGCGATTAC
             51  CG-CCGCGTT CAAACGTGCG AGGGAATC-T ACGGCTATAA CGGCGATTAC 110        120        130        140        150
            101  TTCCTTGTTT CAAACGTGCG AGTTAACCAG CACCGCCGCG TGATTGAGTC
            101  TTCCTTGTTT CAAACGTGCG AGTTAACCAG CACCGCCGCG TGATTGAGTC
            101  TTCCTTGTTT CAAACGTGCG AGTTAACCAG CACCGCCGCG TGATTGAGTC
            101  TTCCTTGTTT CAAACGTGCG AGTTAACCAG CACCGCCGCG TGATTGAGTC 160        170        180        190        200
            151  CCTGATTCAT TCGGGCGAAC CGCTGGGTCT GGAAGCCGGT TCCAAAGCCG
            151  CCTGATTCAT TCGGGCGAAC CGCTGGGTCT GGAAGCCGGT TCCAAAGCCG
            151  CCTGATTCAT TCGGGCGAAC CGCTGGGTCT GGAAGCCGGT TCCAAAGCCG
            151  CCTGATTCAT TCGGGCGAAC CGCTGGGTCT GGAAGCCGGT TCCAAAGCCG 210        220        230        240        250
            201  AGTTGATGGC AGTACTGGCA CATGCTGG-C ATGACCCGTA GCGTCATCGT
            201  AGTTGATGGC AGTACTGGCA CATGCTGG-C ATGACCCGTA GCGTCATCGT
            201  AGTTGATGGC AGTHCTGGCA CATGCTGGHC ATGACCCGTA GCGTCATCGT
            201  AGTTGATGGC AGTACTGGCA CATGCTGG-C ATGACCCGTA GCGTCATCGT 260        270        280        290        300
            251  CTGCAACGGT TATAAAGACC GCGAATATAT CCGCCTGGCA TTAATTGGCG
            251  CTGCAACGGT TATAAAGACC GCGAATATAT CCGCCTGGCA TTAATTGGCG
            251  CTGCAACGGT TATAAAGACC GCGAATATAT CCGCCTGGCA TTAATTGGCG
            251  CTGCAACGGT TATAAAGACC GCGAATATAT CCGCCTGGCA TTAATTGGCG 310        320        330        340        350
            301  AGAAGATGGG GCACAAGGTC TATCTGGTCA TTGAGAAGAT GTCAGAAATC
            301  AGAAGATGGG GCACAAGGTC TATCTGGTCA TTGAGAARAT GTCAVAAATC
            301  AGAAGATGGG GCACAAGGTC TATCTGGTCA TTGAGAAGAT GTCAGAAATC
            301  AGAAGATGGG GCACAAGGTC TATCTGGTCA TTGAGAAGAT GTCAGAAATC 360        370        380        390        400
            351  GCCATTGTGC TGGATGAAGC AGAACGTCTG AATGTCGTTC CTCGTCTGGG
            351  GCCATTGTGC TGGATGAAGC AGDACGTCTG AATGTCGTTC CTCGTCTGGG
            351  GCCATTGTGC TGGATGAAGC AGAACGTCTG AATGTCGTTC CTCGTCTGGG
            351  GCCATTGTGC TGGATGAAGC AGAACGTCTG AATGTCGTTC CTCGTCTGGG 410        420        430        440        450
            401  CGTGCGTGCA CGTCTG---C TTCGCAGGG- TTCGGGTAAA TGGCAGTCCT
            401  CGTGSM-BTC CACCTCTCCC TTCGCAGGGB TTCGGGKAAA WDCCSCTCCT
            401  CGTGVGTGCA CGTCTG---S TTCGCAGGG- TTCGGGTAAA TG-CAGTCCT
            401  CGTGCGTGCA CGTCTGG--C TTCGCAGGG- TTCGGGTAAA TGGCAGTCCT 460        470        480        490        500
            451  CCGGCCCCTG AATG..... .......... .......... ..........
            451  CCGGCCCCTG AATG..... .......... .......... ..........
            451  CCGGCCCCTG AATG..... .......... .......... ..........
            451  CCGGCCCCTG AATG..... .......... .......... ..........
```

Primer PG02

TABLE 6

(SEQ ID NOS: 12–16)

|  | 10 | 20 | 30 | 40 | 50 |
|---|---|---|---|---|---|
| Subject #1 CLONE #7B --- 1 | CATTCAGGGG | CCGGAGGFCG | TTTTGCTACA | GCTGCTGTGG | GCACAATTGC |
| Subject #2 CLONE #8B2 --- 1 | CATTCAGGGG | CCGGAGGFCG | TTTTGCTACA | GCTGCTGTGG | GCACAATTGC |
| Subject #2 CLONE #8B3 --- 1 | CATTCAGGGG | CCGGAGGFCG | TTTTGCTACA | GCTGCTGTGG | GCACAATTGC |
| Subject #3 CLONE #9B2 --- 1 | CATTCAGGGG | CCGGAGGFCG | TTTTGCTACA | GCTGCTGTGG | GCACAATTGC |
| Subject #3 CLONE #9B4 --- 1 | CATTCAGGGG | CCGGAGGFCG | TTTTGCTACA | GCTGCTGTGG | GCACAATTGC |

Primer PG02 marks positions 10–20.

|  | 60 | 70 | 80 | 90 | 100 |
|---|---|---|---|---|---|
| 51 | AGGCGCTGTA | TTAGCACCAA | TCACAAGTGG | TACGGCGTCC | ACTGCTTGGT |
| 51 | AGGCGCTGTA | TTAGCACCAA | TCACAAGTGG | TACGGCGTCC | ACTGCTTGGT |
| 51 | AGGCGCTGTA | TTAGCACCAA | TCACAAGTGG | TACGGCGTCC | ACTGCTTGGT |
| 51 | AGGCGCTGTA | TTAGCACCAA | TCACAAGTGG | TACGGCGTCC | ACTGCTTGGT |
| 51 | AGGCGCTGTA | TTAGCACCAA | TCACAAGTGG | TACGGCGTCC | ACTGCTTGGT |

|  | 110 | 120 | 130 | 140 | 150 |
|---|---|---|---|---|---|
| 101 | CAGGTATCTC | AGGTTCTTCT | AACGCCTTGC | AAGCGTCTAT | GGATGACAAC |
| 101 | CAGGTATCTC | AGGTTCTTCT | AACGCCTTGC | AAGCGTCTAT | GGATGACAAC |
| 101 | CAGGTATCTC | AGGTTCTTCT | AACGCCTTGC | AAGCGTCTAT | GGATGACAAC |
| 101 | CAGGTATCTC | AGGTTCTTCT | AACGCCTTGC | AAGCGTCTAC | GGATGACAAC |
| 101 | CAGGTATCTC | AGGTTCTTCT | AACGCCTTGC | AAGCGTCTAT | GGATGACAAC |

|  | 160 | 170 | 180 | 190 | 200 |
|---|---|---|---|---|---|
| 151 | TTCGCTCAGG | CTGCAGCTGT | ACGTCGCAGA | GCAAGCGTTG | CTGAAGCAGG |
| 151 | TTCGCTCAGG | CTGCAGCTGT | ACGTCGCAGA | GCAAGCGTTG | CTGAAGCAGG |
| 151 | TTCGCTCAGG | CTGCAGCTGT | ACGTCGCAGA | GCAAGCGTTG | CTGAAGCAGG |
| 151 | TTCGCTCAGG | CTGCAGCTGT | ACGTCGCAGA | GCAAGCGTTG | CTGAAGCAGG |
| 151 | TTCGCTCAGG | CTGCAGCTGT | ACGTCGCAGA | GCAAGCGTTG | CTGAAGCAGG |

|  | 210 | 220 | 230 | 240 | 250 |
|---|---|---|---|---|---|
| 201 | AAAAACTGGG | ATTCTGGCGT | ACAGCAATGC | GACTACTCCT | GGATCGAAGG |
| 201 | AAAAACTGGG | ATTCTGGCGT | ACAGCAATGC | GACTACTCCT | GGATCGAAGG |
| 201 | AAAAACTGGG | ATTCTGGCGT | ACAGCAATGC | GACTACTCCT | GGATCGAAGG |
| 201 | AAAAACTGGG | ATTCTGGCGT | ACAGCAATGC | GACTACTCCT | GGATCGAAGG |
| 201 | AAAAACTGGG | ATTCTGGCGT | ACAGCAATGC | GACTACTCCT | GGATCGAAGG |

|  | 260 | 270 | 280 | 290 | 300 |
|---|---|---|---|---|---|
| 251 | TGACTATTGC | GGTTTCTATG | GCTTTTAACT | GCAGCGTTGC | CGGCGCATCT |
| 251 | TGACTATTGC | GGTTTCTATG | GCTTTTAACT | GCAGCGTTGC | CGGCGCATCT |
| 251 | TGACTATTGC | GGTTTCTATG | GCTTTTAACT | GCAGCGTTGC | CGGCGCATCT |
| 251 | TGACTATTGC | GGTTTCTATG | GCTTTTAACT | GCAGCGTTGC | CGGCGCATCT |
| 251 | TGACTATTGC | GGTTTCTATG | GCTTTTAACT | GCAGCGTTGC | CGGCGCATCT |

|  | 310 | 320 | 330 | 340 | 350 |
|---|---|---|---|---|---|
| 301 | GCAGATGCAT | CCAGCTTGCA | GGCAATTGTA | GCGGCACCGG | TCAATATGCC |
| 301 | GCAGATGCAT | CCAGCTTGCA | GGCAATTGCA | GCGGCACCGG | TCAATATGCC |
| 301 | GCAGATGCAT | CCAGCTTGCA | GGCAATTGCA | GCGGCACCGG | TCAATATGCC |
| 301 | GCAGATGCAT | CCAGCTTGCA | GGCAATTGCA | GCGGCACCGG | TCAATATGCC |
| 301 | GCAGATGCAT | CCAGCTTGCA | GGCAATTGCA | GCGGCACCGG | TCAATATGCC |

|  | 360 | 370 | 380 | 390 | 400 |
|---|---|---|---|---|---|
| 351 | TAGTGGTTCA | GCCGTCACAC | CAACATCGTT | TCCGTCGGCT | CCCGTGACAG |
| 351 | TAGTGGTTCA | GCCGTCACAC | CAACATCGTT | TCCGTCGGCT | CCCGTGACAG |
| 351 | TAGTGGTTCA | GCCGTCACAC | CAACATCGTT | TCCGTCGGCT | CCCGTGACAG |
| 351 | TAGTGGTTCA | GCCGTCACAC | CAACATCGTT | TCCGTCGGCT | CCCGTGACAG |
| 351 | TAGTGGTTCA | GCCGTCACAC | CAACATCGTT | TCCGTCGGCT | CCCGTGACAG |

|  | 410 | 420 | 430 | 440 | 450 |
|---|---|---|---|---|---|
| 401 | TTCTTACACA | TTTC | ..... | ..... | ..... |
| 401 | TTCTTACACA | TTTC | ..... | ..... | ..... |
| 401 | TTCTTACACA | TTTC | ..... | ..... | ..... |
| 401 | TTCTTACACA | TTTC | ..... | ..... | ..... |
| 401 | TTCTTACACA | TTTC | ..... | ..... | ..... |

Primer PG03 marks the region at positions 400–413.

TABLE 7

(SEQ ID NO: 17)

Subject #1 CLONE #7A (Primer PG02)

```
         10         20         30         40         50         60
CATTCAGGGG CCGGAGGFGA AAGCCGAGCG ATTTAGGCTG ATGACAACAC ACGGGGTCAG 70         80         90        100        110        120
CGAGCTGGAT GCTGCAATGG TGGTGGCGAG ATCCATAGAC CAAAAGCGGA AATTATCCTG 130        140        150        160        170        180
TCTGACAGCG CTAGCTGTKG ATTTTCAATG ACCTAACAAA TATCAAAGGC CATTCATCCC 190        200        210        220        230        240
AATCACCACT TGATCGAGAC GCTTCACATC GGCGACCCGA CTAACTGAAG AAATATTTTC 250        260        270        280        290        300
GCAATGCTTG ACTTGAGTTG AATTTATCTC CCMCCAATGT TAAAAAGCCA GCGCCTACCC 310        320        330        340        350        360
AGGCTCGCA TTTCTGAGGC GTAAACGCCT CAGCCTTGTA GCGCTTATTC CTTCGACTCT 370        380        390        400        410        420
TCGAGTCGGT TCGCCAGGTG GCCCTTGGCG ATGTTGGAGC CTTGGGCTAG GCACTCAATA 430        440        450        460        470        480
TCAAACACTC AAGGATTATG TGTATGTCGG CGCAGGATGC TGTTGATGAA AATTTGAATA 490        500        510        520        530        540
ACTATTCAAT TACAACCAAC AAAAGAACTT GCCGAGACAC TTAAAACAAA ACCTTCAAAA 550        560        570        580        590        600
ATCTCTTTCT ATGCACACTA TTTACCTGAC AAGAAAAAAT ATAAAACACA TACAATTTCA 610        620        630        640        650        660
AAGCGCGGCG GTGGGGGGCG CCTTATAGAT GCGCCAAACA AAAATCTAAA AATAATTCAA 670        680        690        700        710        720
AGATCTATAG CTAACTTTTT AAACGAACAG TATAAAGCTC GCGCCTGCGT CTTCGCTTAT 730        740        750        760        770        780
GTTCAAAACC GAGGAATAGT AGGTCACGGC GAAGTGCACA CCAATCAAAG ATGGTTACTT 790        800        810        820        830        840
CGATTAGATA TCAAAGATTT CTTCCACTCA ATCACTACTG CACGTTTAAC AGGCCTCCTA 850        860        870        880        890        900
GTTGCCGCAC CGTTTTTCAT TGCCCCGAAT GTAGCAAGAA CTATAAGTTT GCTATGCACT 910        920        930        940        950        960
AAAGACGGGC GCTTACCTCA AGGCTCCCCA GCCAGCCCGA CAATTAGTAA TATTATATGT 970        980        990       1000       1010       1020
CGAGGACTTG ACTACAAGCT CAAAACAATT GCATCTAAAA ATAAGTGTTA CTATACGCGT 1030       1040       1050       1060       1070       1080
TATGCGGACG ACATATTCTT ATCCAATAAC GGCGCGATCT TTCCACCCTT CCTAGCGCAG 1090       1100       1110       1120       1130       1140
AAAAACGATA AAGGCATCGT CACTATTGGA GTGGAGCTTA GTGAAATAAT AACGTCCGCC 1150       1160       1170       1180       1190       1200
GGCTTTAGCA TAAACGAAGA AAAAACTTTT CTCAGAAGTA GGGGCGAACG TCAAATTGTG 1210       1220       1230       1240       1250       1260
ACAGTTCTTA CACATTTC.. .......... .......... .......... ..........
```

(Primer PG03)

TABLE 8

(SEQ ID NOS: 18–20)

Primer PG02

```
                        10         20         30         40         50
Subject #1 CLONE #1B --- 1  AAGCACTTCT GTTTCCAGTA ACAGCGATTG AGGTTTGACC TGGTCATCGG
Subject #2 CLONE #2B --- 1  AAGCACTTCT GTTTCCAGTA ACAGCGATTG AGGTTTGACC TGGTCATCGG
Subject #3 CLONE #3B --- 1  AAGCACTTCT GTTTCCAGTA ACAGCGATTG AGGTTTGACC TGGTCATCGG
                        60         70         80         90        100
                    51  GGCGAAG-TT CCAAGGTGTA GAGCCCAGCT GGACCAAGGC TTGGGCTATC
                    51  GGCGAAGCTT CCAAGGTGTA GAGCCCAGCT GGACCAAGGC TTGGGCTATC
                    51  GGCGAAG-TT CCAAGGTGTA GAGCCCAGCT GGACCAAGGC TTGGGCTATC
                       110        120        130        140        150
                   101  TGCTCATGCT CGAGCGGGTT GCAAACCAGG GTGGCCTTCA TAGGTGGAAT
                   101  TGCTCATGCT CGAGCGGGTT GCAAACCAGG GTGGCCTTCA TAGGTGGAAT
                   101  TGCYCATGCT CGAGCGGGTT GCAAACCAGG GTGGCCTTCA TAGGTGGAAT
                       160        170        180        190        200
                   151  TTGCGTCGTT ACCAACTGTT TGACCAATGC CGAAAGG-GC TTTGGGGGAG
                   151  TTGCGTCGTT ACCAACTGTT TGACCAATGC CGAAAGGCGC TTTGGGGGAG
                   151  TTGCGTCGTT ACCAACTGTT TGSCCAATGC CGAAAGGCGC TTTGGGGGAG
                       210        220        230        240        250
                   201  GCACTTCCTC CAACAGGCAG TGGAAGGCTC GGTTGGCGAT GGATGTTGCG
                   201  GCACTTCCTC CAACAGGCAG TGGAAGSCTC GGTTGGCGAT GGATGTTGCG
                   201  GCACTTCCTC CAACAGGCAG TGGAAGGCTC GGTTGGCGAT GGATGTTGCG
                       260        270        280        290        300
                   251  TAGTGTTCGA GGTTGTCACA CATCGCCTTG CGTTGGCGCB CCCACGCACT
                   251  TAGTGTTCGA GGTTGTCACA CATCGCCTTG CGTTGGCGCT CCCACGCACT
                   251  TAGTGTTCGA GGTTGTCACA CATCGCCTTG CGTTGGCGCY CCCACGCACT
                       310        320        330        340        350
                   301  GAGTTGCGCG TGGGCGCGTG ACCAGAAGTC ACCAGAAGTC TKCTCAAGCA
                   301  GAGTTGCGCG TGGGCGCGTG ACCAGAAGTC ACCAGAAGTC TGCTCAAGCA
                   301  GAGTTGCGCG TGGGCGCGTG ACCAGAAGTC ACCAGAAGTC TGCTCAAGCA
                       360        370        380        390        400
                   351  TTTCTTCACG ATGCTCAACC GCCTGGCGCA GAGGCTCTTC AGCTTGGGCC
                   351  TTTCTTCACG ATGCTCAACC GCCTGGCGCA GCAGCTCTTC AGCTTGGGCC
                   351  TTTCTTCACG ATGCTCAACC GCCTGGCGCA GCAGCTCTTC AGCTTGGGCC
                       410        420        430        440        450
                   401  CGTGCGCTAT CTAGCAACTG CGCGGACTGA AAGCAATCGG CGAGCATCTC
                   401  CGTGCGCTAT CTAGCAACTG CGCGGACTGA AAGCAATCGG CGAGCATCTC
                   401  CGTGCGCTAT CTAGCAACTG CGCGGACTGA AAGCAATCGG CGAGCATCTC
                       460        470        480        490        500
Subject #1 CLONE #1B --- 451  CCGGGTAATC AGTACTTTTG GCTGCCCGGA AGCGCCGTCG TGCAATTCGA
Subject #2 CLONE #2B --- 451  CCGGGTAATC AGTACTTTTG GCTGCCCGGA AGCGCCGTCG TGCAATTCGA
Subject #3 CLONE #3B --- 451  CCGGGTAATC AGTACTTTTG GCTGCCCGGA AGCGCCGTCG TGCAATTCGA
                       510        520        530        540        550
                   501  TTTTGCGTTG GGTCAACATA GACAATGCTC TGGTGTGTTG CCGTTAACGA
                   501  TTTTGCGTTG GGTCAACATA GACAATGCTC TGGTGTGTTG CCGTTAACGA
                   501  TTTTGCGTTG GGTCAACATA GACAATGCTC TGGTGTGTTG CCGTTAACGA
                       560        570        580        590        600
                   551  CGAGTTGTTT CACTACCCGT TGCGTCGATA CGCCAGACAA TCGCCTGCCA
                   551  CGAGTTGTTT CACTACCCGT TGCGTCGATA CGCCAGACAA TCGCCTGCCA
                   551  CGAGTTGTTT CACTACCCGT TGCGTCGATA CGCCAGACAA TCGCCTGCCA
                       610        620        630        640        650
                   601  CAGCGTATTG AGCCGGCCAT GCGCATCGTC AAATGGCAGG TGTGTGGTTT
                   601  CAGCGTATTG AGCCGGCCAT GCGCATCGTC AAATGGCAGG TGTGTGGTTT
                   601  CAGCGTATTG AGCCGGCCAT GCGCATCGTC AAATGGCAGG TGTGTGGTTT
```

TABLE 8-continued (SEQ ID NOS: 18–20)

```
              660        670        680        690        700
651  CAAGTGCCTG CACCCGGTCA GGCGGCAAGC GCAGACGAAG GCGTTGCCAG
651  CAAGTGCCTG CACCCGGTTA GGCGGCAAGC GCAGACGAAG GCGTTGCCAG
651  CAAGTGCCTG CACCCGGTCA GGCGGCAAGS GCAGACGAAG GCGTTGCCAG 710        720        730        740        750
701  ACAGCAGGCT CGACCCAGGC CCTCAGCAAT TGCATTGGAT CATCCTCCGG
701  ACAGCAGGCT CGACCCAGGC CCTCAGCAAT TGCATTGGAT CATCCTCCGG
701  ACAGCAGGCT CGACCCAGGC CCTCAGCAAT TGCATTGGAT CATCCTCCGG 760        770        780        790        800
751  CCCCTGAATG .......... .......... .......... ..........
751  CCCCTGAATG .......... .......... .......... ..........
751  CCCCTGAATG .......... .......... .......... ..........
```

(Primer PG03)

TABLE 9

(SEQ ID NO: 21)

```
Subject #2 CLONE #5B (Primer PG03)

10         20         30         40         50         60
   GAAATGTGTA AGAACTGTCA TGCCTGCGTA AGGTTGCTCC GACAGATGTA ACCTCCCATG 70         80         90        100        110        120
   GAAATGTGAC ATTTTACTGC GGCGCCGCTT GTTCATCGGC GCCAAAGTCC CGGCACCGCC 130        140        150        160        170        180
   CTCGCAGAAA TGATTAATAA ACAATCAATA AAGGGCTATT AACCCCGAGC AATGCTAAAC 190        200        210        220        230        240
   TGAGGCTCCT TACATCTACC CGGTGAAAGA TATGTCTATC TTTGATGCCC TTAAGATGTT 250        260        270        280        290        300
   CAGCGACTCA TCAGTAAAAG TGACCTGCCC GAAATGCGCT CACGTATCTG AACAAAACAG 310        320        330        340        350        360
   TCGCAAAATG CGTAAAAACA TCACCATGAT CTGCCCTAAA TGSCGGCACT ATTTCCTTCC 370        380        390        400        410        420
   TGACGACAAC TAACGCCTTT CTCTTTCTCT GCTGCAGTGT CAAACGCAAG CGTAACGTCA 430        440        450        460        470        480
   CTGTTTATCC GGCAAGCGAG CCAACAGCAG TTCTCGCCGC CGTCCGCTGA AATACTTCAG 490        500        510        520        530        540
   CATCAGCGCC AGGCAAACCA ACCAGGCAGG GATCAGCAAC AGGCTAAAAG AAACATTGTT 550        560        570        580        590        600
   AC........ .......... .......... .......... .......... ..........
```

(Primer PG04)

TABLE 10
(SEQ ID NO: 22)
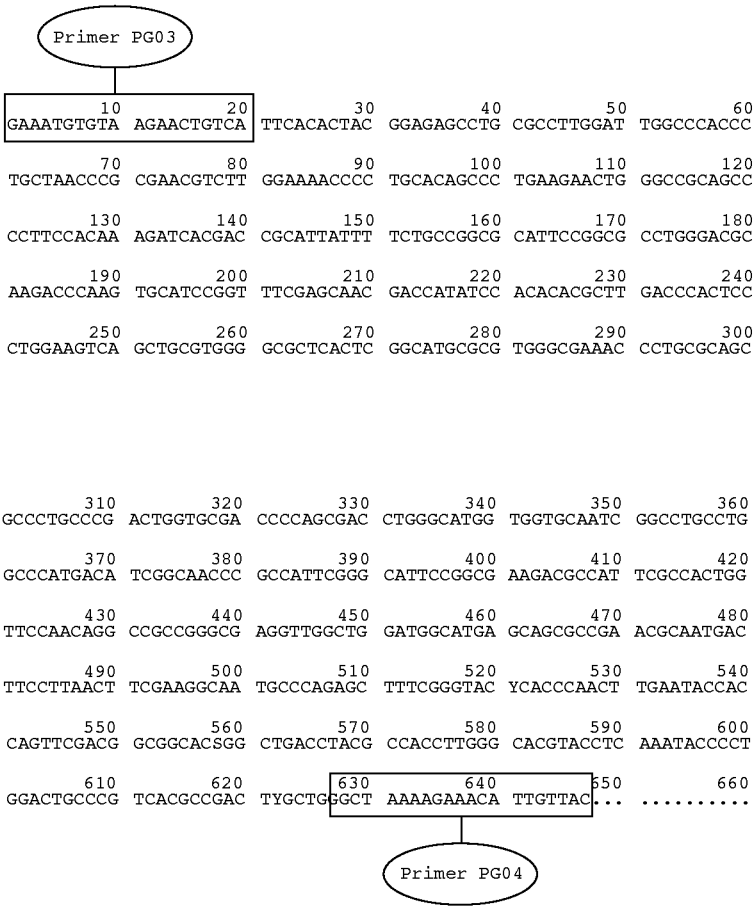

TABLE 11

SEQ ID NO: 23 (Clone 60)
SEQ ID NO: 24 (Clone 61)
SEQ ID NO: 25 (Clone 62)
SEQ ID NO: 26 (Clone 64)

```
                    10                  20                  30                  40
  1  AAGCACTTCTGTTTCCTGAATCTAAAGAAAGACAACATGC   CLONE 60
  1  AAGCACTTCTGTTTCCTGAATCTAAAGAAAGACAACATGC   CLONE 61
  1  AAGCACTTCTGTTTCCTGAATCTAAAGAAAGACAACATGC   CLONE 62
  1  AAGCACTTCTGTTTCCTGAATCTAAAGAAAGACAACATGC   CLONE 64

50                  60                  70                  80
 41  TGCTTTTTAATCATAGGATGGAGAATTTTAAAGAACTGTT   CLONE 60
 41  TGCTTTTTAATCATAGGATGGAGAATTTTAAAGAACTGTT   CLONE 61
 41  TGCTTTTTAATCATAGGATGGAGAATTTTAAAGAACTGTT   CLONE 62
 41  TGCTTTTTAATCATAGGATGGAGAATTTTAAAGAACTGTT   CLONE 64

90                 100                 110                 120
 81  TGGGCCAGGCACAGTCGCTCATACTTGTAATCCCAGCACT   CLONE 60
 81  TGGGCCAGGCACAGTCGCTCATACTTGTAATCCCAGCACT   CLONE 61
 81  TGGGCCAGGCACAGTCGCTCATACTTGTAATCCCAGCACT   CLONE 62
 81  TGGGCCAGGCACAGTCGCTCATACTTGTAATCCCAGCACT   CLONE 64

130                 140                 150                 160
121  TTGGGAGGCCGAGGCGGGTGGATCACAAGGTCAGCAGATC   CLONE 60
121  TTGGGAGGCCGAGGCGGGTGGATCACAAGGTCAGCAGATC   CLONE 61
121  TTGGGAGGCCGAGGCGGGTGGATCACAAGGTCAGCAGATC   CLONE 62
121  TTGGGAGGCCGAGGCGGGTGGATCACAAGGTCAGCAGATC   CLONE 64

170                 180                 190                 200
161  GAGACCATCCTGGCCAACATGGTGAAACCCTGTCTCTACT   CLONE 60
161  GAGACCATCCTGGCCAACATGGTGAAACCCTGTCTCTACT   CLONE 61
161  GAGACCATCCTGCCAACATGGTGAAACCCTGTCTCTACT    CLONE 62
161  GAGACCATCCTGGCCAACATGGTGAAACCCTGTCTCTACT   CLONE 64

210                 220                 230                 240
201  AAAAATACAAAAATTAGCCGGGTGTGGTGGCACATGCCTG   CLONE 60
201  AAAAATACAAAAATTAGCCGGGTGTGGTGGCACATGCCTG   CLONE 61
201  AAAAATACAAAAATTAGCCGGGTGTGGTGGCACATGCCTG   CLONE 62
201  AAAAATACAAAAATTAGCCGGGTGTGGTGGCACATGCCTG   CLONE 64

250                 260                 270                 280
241  TAATCCCAGCTACTCGGGAAGCTGAGGCAGGAGAATTGCT   CLONE 60
241  TAATCCCAGCTACTCGGGAAGCTGAGGCAGGAGAATTGCT   CLONE 61
241  TAATCCCAGCTACTCGGGAAGCTGAGGCAGGAGAATTGCT   CLONE 62
241  TAATCCCAGCTACTCGGGAAGCTGAGGCAGGAGAATTGCT   CLONE 64

290                 300                 310                 320
281  TGAACCAGGGAGTTGGAGGTTGCAGTGAGCTAAGACTGCA   CLONE 60
281  TGAACCAGGGAGTTGGAGGTTGCAGTGAGCTAAGACTGCA   CLONE 61
281  TGAACCAGGGAGTTGGAGGTTGCAGTGAGCTAAGACTGCA   CLONE 62
281  TGAACCAGGGAGTTGGAGGTTGCAGTGAGCTAAGACTGCA   CLONE 64
```

TABLE 11-continued

SEQ ID NO: 23 (Clone 60)
SEQ ID NO: 24 (Clone 61)
SEQ ID NO: 25 (Clone 62)
SEQ ID NO: 26 (Clone 64)

```
              330        340        350        360
              |          |          |          |
321  CCACTGCACTCCAGCCCTGGTGACAGAACGAGACTCTGTCT   CLONE 60
321  CCACTGCACTCCAGCCCTGGTGACAGAACGAGACTCTGTCT   CLONE 61
321  CCACTGCACTCCAGCCCTGGTGACAGAACGAGACTCTGTCT   CLONE 62
321  CCACTGCACTCCAGCCCTGGTGACAGAACGAGACTCTGTCT   CLONE 64

370        380        390        400
              |          |          |          |
361  TAAAAACAAACAAACAAAAAAAAAATCTGTTAGATAGGCT    CLONE 60
361  TAAAAACAAACAAACAAAAAAAAAATCTGTTAGATAAGCT    CLONE 61
361  TAAAAACAAACAAACAAAAAAAAAATCTGTTAGATAAGCT    CLONE 62
361  TAAAAACAAACAAACAAAAAAAAAATCTGTTAGATAAGCT    CLONE 64

410        420        430        440
              |          |          |          |
401  ATCAAAATGCAGCTGTTGTTTTGTTTTTGGCTCACTGTTT    CLONE 60
401  ATCAAAATGCAGCTGTTGTTTTGTTTTTGGCTCACTGTTT    CLONE 61
401  ATCAAAATGCAGCTGTTGTTTTGTTTTTGGCTCACTGTTT    CLONE 62
401  ATCAAAATGCAGCTGTTGTTTTGTTTTTGGCTCACTGTTT    CLONE 64

450        460        470        480
              |          |          |          |
441  TCGTGGTTGTAACTAATATGTGGAAAGGCCCATTTCCAGG    CLONE 60
441  TCGTGGCTGTAACTAATATGTGGAAAGGCCCATTTCCAGG    CLONE 61
441  TCGTGGTTGTAACTAATATGTGGAAAGGCCCATTTCCAGG    CLONE 62
441  TCGTGGTTGTAACTAATATGTGGAAAGGCCCATTTCCAGG    CLONE 64

490        500        510        520
              |          |          |          |
481  TTTGCCGTAGAAGAGCCCAGAAAACAGAGTCTCAAGACCC    CLONE 60
481  TTTGCCGTAGAAGAGCCCAGAAAACAGAGTCTCAAGACCC    CLONE 61
481  TTTGCCGTAGAAGAGCCCAGAAAACAGAGTCTCAAGACCC    CLONE 62
481  TTTGCCGTAGAAGAGCCCAGAAAACAGAGTCTCAAGACCC    CLONE 64

530        540        550        560
              |          |          |          |
521  CGCTCTGGACTGTCATAAGCTAGCACCCGTGGTAAGCGGG    CLONE 60
521  CGCTCTGGACTGTCATAAGCTAGCACCCGTGGTAAGCGGG    CLONE 61
521  CGCTCTGGACTGTCATAAGCTAGCACCCGTGGTAAGCGGG    CLONE 62
521  CGCTCTGGACTGTCATAAGCTAGCACCCGTGGTAAGCGGG    CLONE 64

570        580        590        600
              |          |          |          |
561  ACGAGACAAGCTCCCGAAGCCCGCCAGCTTCCTGCTCCAC    CLONE 60
561  ACGAGACAAGCTCCCGAAGCCCGCCAGCTTCCTGCTCCAC    CLONE 61
561  ACGAGACAAGCTCCCGAAGCCCGCCAGCTTCCTGCTCCAC    CLONE 62
561  ACGAGACAAGCTCCCGAAGCCCGCCAGCTTCCTGCTCCAC    CLONE 64

610        620        630        640
              |          |          |          |
601  TCAGCTCCGTCCAGTCAACCTGAACCCACCCAGTCCAGCT    CLONE 60
601  TCAGCTCCGTCCAGTCAACCTGAACCCACCCAGTCCAGCT    CLONE 61
601  TCAGCTCCGTCCAGTCAACCTGAACCCACCCAGTCCAGCT    CLONE 62
601  TCAGCTCCGTCCAGTCAACCTGAACCCACCCAGTCCAGCT    CLONE 64

650        660        670        680
              |          |          |          |
641  GTCTGTGGGAATGGTGGTGTTCTTAGGGACAGACTGACAC    CLONE 60
641  GTCTGTGGGAATGGTGGTGTTCTTAGGGACAGACTGACAC    CLONE 61
641  GTCTGTGGGAATGGTGGTGTTCTTAGGGACAGACTGACAC    CLONE 62
641  GTCTGTGGGAATGGTGGTGTTCTTAGGGACAGACTGACAC    CLONE 64

690        700        710
              |          |          |
681  CTTACTTGTCAGTGTTCCTCCGGCCCCTGAATG           CLONE 60
681  CTTACTTGTCAGTGTTCCTCCGGCCCCTGAATG           CLONE 61
681  CTTACTTGTCAGTGTTCCTCCGGCCCCTGAATG           CLONE 62
681  CTTACTTGTCAGTGTTCCTCCGGCCCCTGAATG           CLONE 64
```

What is claimed is:

1. A method of detecting the presence of a target human nucleic acid in an acellular biological sample from a patient, the method comprising:
providing the acellular biological sample;
contacting the sample with a nucleic acid probe which specifically hybridizes to the target human nucleic acid, wherein the target human nucleic acid is an RNA molecule comprising sequences transcribed from human germline DNA, and wherein the nucleic acid probe is selected from a) a nucleic acid probe consisting of SEQ ID NO:1, SEQ ID NO:2, SEQ ID NO:3, or SEQ ID NO:4; and b) a nucleic acid probe that hybridizes under stringent conditions of 0.2×SSC at about 60° C. to SEQ ID NO:18, SEQ ID NO:19, SEQ ID NO:20, SEQ ID NO:23, SEQ ID NO:24, SEQ ID NO:25, or SEQ ID NO:26; and
detecting a hybridization complex comprising the nucleic acid probe as indicative of the presence of the target human nucleic acid in the acellular biological sample.

2. The method of claim 1, wherein the RNA molecule comprises sequences transcribed from a fragile site in human germline DNA.

3. The method of claim 1, wherein the RNA molecule comprises sequences transcribed from repetitive DNA in human germline DNA.

4. The method of claim 1, wherein the target human nucleic acid comprises chimeric nucleic acid sequences.

5. The method of claim 3, wherein the repetitive DNA comprises Alu sequences.

6. he method of claim 1, wherein the target human nucleic acid is at least about 100 nucleotides in length.

7. The method of claim 6, wherein the target human nucleic acid is between about 500 and about 1500 nucleotides in length.

8. The method of claim 1, wherein the acellular biological sample is blood plasma.

9. The method of claim 1, wherein the acellular biological sample is obtained from a patient undergoing treatment for a disease.

10. The method of claim 1, wherein the acellular biological sample is obtained from a patient suspected of suffering from a disease.

11. The method of claim 10, wherein the disease is a chronic illness.

12. The method of claim 11, wherein the chronic illness is cancer.

13. The method of claim 12, wherein the cancer is multiple myeloma.

14. The method of claim 11, wherein the chronic illness is a neurodegenerative disease.

15. The method of claim 1, wherein the step of contacting includes a step of amplifying the target human nucleic acid.

16. The method of claim 15, wherein the step of amplification is carried out using a polymerase chain reaction (PCR).

17. The method of claim 16, wherein the step of amplification comprises amplifying the target human nucleic acid using a primer consisting of SEQ ID NO:1.

18. The method of claim 16, wherein the step of amplification comprises amplifying the target human nucleic acid using a primer consisting of SEQ ID NO:2.

19. The method of claim 1, wherein the acellular biological sample is serum.

20. The method of claim 11, wherein the patient is a veteran of the Persian Gulf War.

21. The method of claim 1, wherein the nucleic acid which specifically hybridizes to the target human nucleic acid is linked to a solid support.

* * * * *